United States Patent
Duefel et al.

(10) Patent No.: US 9,637,774 B2
(45) Date of Patent: May 2, 2017

(54) GLYCOSYLATED MODIFIED FLAVIN ADENINE DINUCLEOTIDE-DEPENDENT GLUCOSE DEHYDROGENASES, COMPOSITIONS THEREOF AS WELL AS METHODS OF MAKING AND USING THE SAME

(71) Applicant: Roche Diabetes Care, Inc., Indianapolis, IN (US)

(72) Inventors: Hartmut Duefel, Schlehdorf (DE); Thomas Meier, Munich (DE); Michael Tacke, Munich (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 131 days.

(21) Appl. No.: 14/527,887

(22) Filed: Oct. 30, 2014

(65) Prior Publication Data

US 2015/0064733 A1   Mar. 5, 2015

Related U.S. Application Data

(63) Continuation of application No. PCT/EP2013/059313, filed on May 3, 2013.

(30) Foreign Application Priority Data

May 3, 2012 (EP) .................................. 12166703

(51) Int. Cl.
  *C12Q 1/54* (2006.01)
  *C12N 9/00* (2006.01)
  *C12N 9/04* (2006.01)

(52) U.S. Cl.
  CPC ............ *C12Q 1/54* (2013.01); *C12N 9/0006* (2013.01); *C12Y 101/9901* (2013.01); *C12Y 101/05* (2013.01)

(58) Field of Classification Search
  None
  See application file for complete search history.

(56) References Cited

U.S. PATENT DOCUMENTS

| 2008/0220460 A1 | 9/2008 | Kawaminami et al. |
| 2008/0248514 A1* | 10/2008 | Inamori ............... C12N 9/0006 435/26 |
| 2011/0045513 A1 | 2/2011 | Takenaka et al. |

FOREIGN PATENT DOCUMENTS

EP    2241621 A1    10/2010

OTHER PUBLICATIONS

International Search Report issued Sep. 19, 2013 in Application No. PCT/EP2013/059313, 5 pages.
Sygmund, Christoph et al., "Heterologous overexpression of Glomerella cingulata FAD-dependent glucose dehydrogenase in *Escherichia coli* and Pichia pastoris," Microbial Cell Factories, 2011, 9 pages.
Zafar, Muhammad Nadeem et al., "Characterization of different FAD-dependent glucose dehydrogenases for possible use in glucoase-based biosensors and biofuel cells," Analytical and Bioanalytical Chemistry, Feb. 2012, pp. 2069-2077, vol. 402, No. 6.

* cited by examiner

*Primary Examiner* — Suzanne M Noakes
*Assistant Examiner* — Jae W Lee

(57) ABSTRACT

Compositions, devices, kits and methods are disclosed for assaying glucose with a glycosylated, modified flavin adenine dinucleotide-dependent glucose dehydrogenase (FAD-GDH), variant thereof or an active fragment thereof, where at least one asparagine residue at positions N2, N168 and N346 of mature, wild-type *A. oryzae* FAD-GDH according to SEQ ID NO:2 is substituted by one or more amino acids not suitable for glycosylation, thereby eliminating or inactivating, respectively, a potential glycosylation site at this position.

18 Claims, 3 Drawing Sheets

GLYCOSYLATED MODIFIED FLAVIN ADENINE DINUCLEOTIDE-DEPENDENT GLUCOSE DEHYDROGENASES, COMPOSITIONS THEREOF AS WELL AS METHODS OF MAKING AND USING THE SAME

CROSS-REFERENCE TO RELATED APPLICATIONS

This patent application is a continuation of Int'l Patent Application No. WO PCT/EP2013/059313 (filed 3 May 2013), which claims priority to and the benefit of EP Patent Application No. 12166703.4 (filed 3 May 2012). Each patent application is incorporated herein by reference as if set forth in its entirety.

REFERENCE TO SEQUENCE LISTING SUBMITTED ELECTRONICALLY

An official copy of a Sequence Listing is submitted electronically via EFS-Web as an ASCII-formatted Sequence Listing with a file named "30776SequenceListing.txt," created on 28 Oct. 2014, and having a size of 49.8 KB. The Sequence Listing is filed concurrently with the Specification, is a part thereof and is incorporated herein by reference as if set forth in its entirety.

TECHNICAL FIELD

This disclosure relates generally to chemistry, medicine and molecular biology, and more particularly, it relates to glycosylated, modified flavin adenine dinucleotide-dependent glucose dehydrogenases (FAD-GDHs) having improved temperature stability under dry conditions that can be used in test elements for measuring glucose, as well as methods of making and using the same.

BACKGROUND

Self-monitoring of blood glucose is important for individuals with diabetes to be aware of their usual glucose levels and to use them for treatment. Enzymes having glucose substrates are employed in sensors for self-monitoring of blood glucose. One such enzyme is glucose oxidase (EC 1.1.3.4), which has an advantage of being highly specific to glucose and having high heat stability. For this reason, it has been used as an enzyme in blood glucose sensors. The first announcement of such properties goes back to as long as forty years ago. In blood glucose sensors that utilize glucose oxidase, the blood glucose level is measured when electrons generated in the process of converting glucose to D-glucono-d-lactone by oxidization are conducted to an electrode via a mediator. However, glucose oxidase poses a problem in that it tends to transfer protons produced by the reaction to oxygen, causing dissolved oxygen to adversely affect the measured values.

One solution to address this problem is to use a nicotinamide adenine dinucleotide (NAD)- or NAD phosphate (NADP)-dependent glucose dehydrogenase (EC 1.1.1.47) or pyrroloquinoline quinone (PQQ)-dependent glucose dehydrogenase (EC1.1.5.2; formerly EC1.1.99.17) as the enzyme in blood glucose sensors. These enzymes have an advantage of being free from the influence of dissolved oxygen. However, NAD(P)-dependent glucose dehydrogenases have poor stability and are cumbersome, often requiring a coenzyme. Similarly, PQQ-dependent glucose dehydrogenases have poor substrate specificity and react to saccharides other than glucose, such as maltose and lactose, thereby deteriorating the accuracy of the measurement values.

WO Patent Application Publication No. 2004/058958 discloses an *Aspergillus*-derived, flavin-bound glucose dehydrogenase. Since the activity of this enzyme on xylose is only 10% of that on glucose, in the case of measuring the blood glucose level of an individual taking a xylose tolerance test, the accuracy of the measured value may be impaired. In addition, the enzyme has a residual activity ratio of about 89% after treatment at 50° C. for 15 minutes, thereby exhibiting good heat stability. Moreover, WO Patent Application Publication No. 2006/101239 discloses nucleic acid and amino acid sequences of the enzyme.

U.S. Pat. No. 7,662,600 discloses a modified FAD-GDH having improved heat stability in liquid when compared to an FAD-GDH derived from wild-type FAD-GDH. The modified FAD-GDH is derived from a eukaryote, especially a filamentous fungus such as an *Aspergillus* spp., and as having a primary structure with at least one amino acid substituted, deleted, inserted or added to FAD-GDH.

US Patent Application Publication No. 2008/220460 discloses a modified FAD-GDH derived from an *Aspergillus* spp. (e.g., *Aspergillus oryzae* or *Aspergillus terreus*) having improved heat stability when compared to wild-type FAD-GDHs. This reference focuses only on a modified FAD-GDH produced by gene recombination in *Escherichia coli*. Consequently, the FAD-GDHs are non-glycosylated enzyme variants that were screened only under liquid conditions. The reference therefore is silent about specific modifications to the nucleotide sequence to obtain FAD-GDH variants that are glycosylated and that have improved heat stability under dry conditions by eliminating or inactivating a potential glycosylation site.

For some uses of FAD-GDHs, the heat stability under dry conditions is of special importance. For instance, and with respect to test elements for blood-glucose measurements, the enzyme properties of FAD-GDH in dry chemistries needs to be improved.

BRIEF SUMMARY

An inventive concept described herein are enzymes, in particular, glycosylated, modified FAD-GDHs having improved temperature stability under dry conditions. This concept is achieved by substituting at least one asparagine (Asn or N) residue in a wild-type, mature *A. oryzae* FAD-GDH sequence with one or more amino acids not suitable for glycosylation, thereby eliminating or inactivating, respectively, a potential glycosylation site at at least one of these positions. The disclosure therefore describes various glycosylated, modified FAD-GDHs, and it was surprisingly found that a certain type of variant exhibits improved temperature stability under dry conditions while substantially retaining dehydrogenase activity.

In one aspect, glycosylated, modified FAD-GDHs are provided that have improved temperature stability under dry conditions. The FAD-GDHs are modified so that at least one of the Asp residues at positions N2, N168 and N346 of mature, wild-type *A. oryzae* FAD-GDH according to SEQ ID NO:2 has been substituted by one or more amino acids not suitable for glycosylation, thereby eliminating or inactivating a potential glycosylation site at one or more of these positions. Also provided are variants and active (functional) fragments thereof. Moreover, the glycosylated, modified FAD-GDHs as described herein exhibit an improved temperature stability under dry conditions when compared to a reference glycosylated FAD-GDH.

When the glycosylated, modified FAD-GDHs are variants (i.e., functional equivalents) or active fragments thereof, they exhibit at least about 80% amino acid sequence identity or more (e.g., about 90% or even about 95%) to the glycosylated, modified FAD-GDHs described above, provided that the variants or active fragments thereof include at least one of the Asp substitution(s) when compared to the mature, wild-type FAD-GDH and provided that the variants or the active fragments thereof exhibit at least about 80% or more of the enzyme activity of the glycosylated, modified FAD-GDHs described above and exhibit at least about 80% or more of the temperature stability under dry conditions of the glycosylated, modified FAD-GDHs described above.

In some instances, the glycosylated, modified FAD-GDH has a sequence according to SEQ ID NO:3, where the Asn residue at position 2 of mature, wild-type FAD-GDH is replaced by a serine (Ser or S) residue. Alternatively, the glycosylated, modified FAD-GDH has a sequence according to SEQ ID NO:5, where the Asn residue at position 168 of mature, wild-type FAD-GDH is replaced by two amino acids, namely a Ser residue and a proline (Pro or P) residue. Alternatively still, the glycosylated, modified FAD-GDH has a sequence according to SEQ ID NO:6, where the Asn residue at position 346 of mature, wild-type FAD-GDH is replaced by an aspartic acid (Asp or D) residue. In other instances, the glycosylated, modified FAD-GDH has two or more of these substitutions, which further can include a sequence according to SEQ ID NO:4, where the Asn residue at position 168 of mature, wild-type FAD-GDH is replaced by a Pro residue.

In some instances, the glycosylated, modified FAD-GDHs, variants and/or fragments thereof exhibit an improved temperature stability under dry conditions when compared to a glycosylated FAD-GDH according to SEQ ID NO:1, where the FAD-GDH according to SEQ ID NO:1 is obtained by expression in *A. oryzae*.

In another aspect, isolated nucleic acid sequences/polynucleotides are provided that encode the glycosylated, modified FAD-GDHs, variants and/or active fragments thereof.

In another aspect, vectors are provided that include at least one nucleic acid sequence/polynucleotide encoding the glycosylated, modified FAD-GDHs, variants and/or active fragments thereof.

In another aspect, host cells are provided that are transformed with at least one vector as described herein.

In another aspect, a device is provided for assaying glucose in a sample, where the device includes a glycosylated, modified FAD-GDH, variant and/or active fragment thereof and optionally an electron mediator.

In another aspect, a kit is provided for assaying glucose in a sample, where the kit includes a glycosylated, modified FAD-GDH, variant and/or active fragment thereof and optionally an electron mediator.

In view of the foregoing, the methods of making the glycosylated, modified FAD-GDHs as described herein are provided. The methods can include culturing a transformant/host cell, and then collecting and purifying the glycosylated, modified FAD-GDH, variant and/or active fragment thereof as described herein from the culture.

In another aspect, methods are provided for using the glycosylated, modified FAD-GDHs, variants and/or active fragments thereof. The methods can include contacting the sample with glycosylated, modified FAD-GDH, variant and/or active fragment thereof and then measuring an amount of glucose oxidized thereby. In some instances, the glycosylated, modified FAD-GDH, variant and/or active fragment thereof is incorporated into a device such as a biosensor test strip, enzyme electrode or sensor as described herein.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein.

Figure 1:
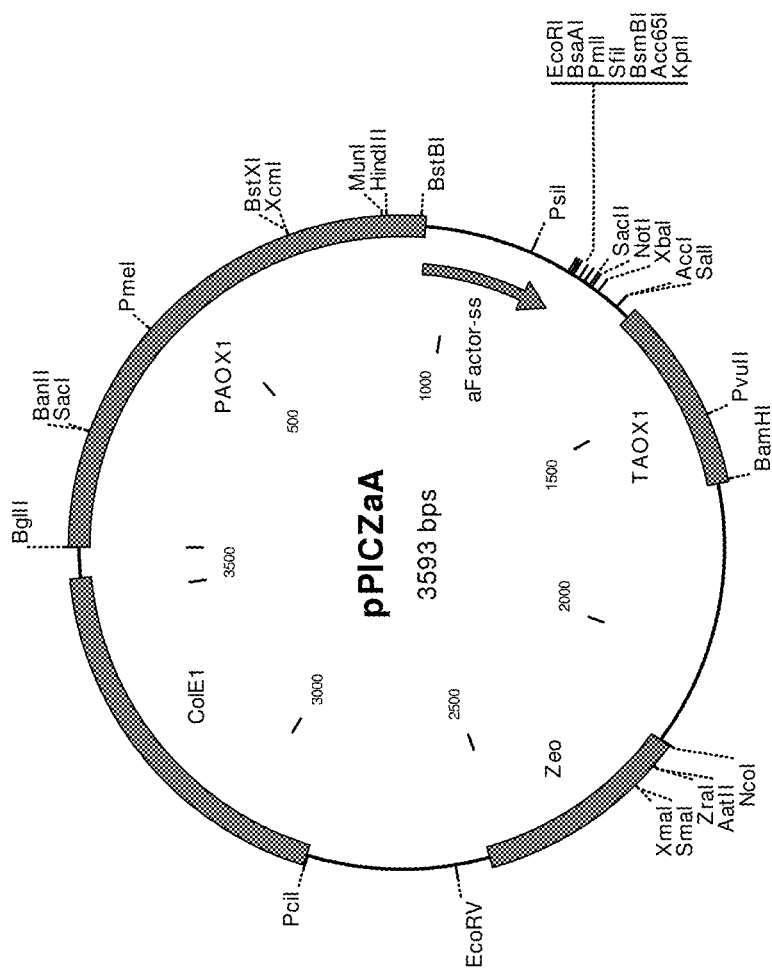
FIG. 1 shows an exemplary *Pichia* expression vector, pPICZαA. PAOX1=AOX1 promoter (initiates transcription of the gene of interest); αFactor-ss=gene encoding the α-Factor signal sequence (gene of interest is fused in frame to this sequence; corresponding polypeptide is secreted into the culture medium by *P. pastoris*); TAOX1=AOX1 terminator (stops transcription of the gene of interest); Zeo=Zeomycin resistance gene-selection marker; and ColE1=origin of replication (allows cloning in *E. coli*).

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The compositions, devices, kits and methods now will be described more fully hereinafter with reference to the accompanying drawings, in which some, but not all embodiments of the inventive concept are shown. Indeed, the compositions, devices, kits and methods may be embodied in many different forms and should not be construed as limited to the embodiments set forth herein; rather, these embodiments are provided so that this disclosure will satisfy applicable legal requirements.

Likewise, many modifications and other embodiments of the compositions, devices, kits and methods described herein will come to mind to one of skill in the art to which the disclosure pertains having the benefit of the teachings presented in the foregoing descriptions and the associated drawings. Therefore, it is to be understood that the compositions, devices, kits and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the compositions, devices, kits and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) or to a situation in which, besides B, one or more further elements are present in A, such as element C, elements C and D, or even further elements.

Overview

Exemplary compositions, devices, kits and methods are provided for measuring glucose and are based upon glycosylated, modified FAD-GDHs having a substitution of at least one of the Asn residues at positions N2, N168 and N346 of mature, wild-type *A. oryzae* FAD-GDH according to SEQ ID NO:2 by one or more amino acids not suitable for glycosylation and thereby eliminating or inactivating a potential glycosylation site at this position. Such compositions, devices, kits and methods incorporating a glycosylated, modified FAD-GDH, variant and/or active fragment thereof are useful in a variety of applications. For example, they may be used for measuring glucose, which is clinically useful in diagnosing and controlling diabetic conditions.

As used herein, "mature," in relation to sequence(s) herein, means a raw sequence format of the respective amino acid/protein sequence(s) without any added signaling sequences (e.g., signal peptides or equivalents thereof).

The present inventive concept therefore provides FAD-GDH enzymes, nucleic acid sequences encoding such enzymes, vectors including the nucleic acid sequences, host cells incorporating the vectors, compositions thereof and methods for monitoring blood glucose in individuals, especially individuals having diabetes. Advantageously, the glycosylated, modified FAD-GDHs, variants and/or active fragments thereof exhibit improved temperature stability under dry conditions when compared to a reference glycosylated FAD-GDH.

As used herein, "temperature stability" means an ability of the glycosylated, modified FAD-GDHs as described herein to resist changes in terms of its native biophysical and biochemical properties as its temperature changes, in particular, temperature increases. With this context, 100% temperature stability would reflect that no changes occur to the native biophysical and biochemical properties when compared to the enzyme before exposure to temperature over a certain period of time (t) with respect to particularly defined properties of the enzyme. Thus, the glycosylated, modified FAD-GDHs, variants or active fragments thereof preserve native enzyme activity during exposure to temperature over a certain period of time (t), and exemplarily exhibit an enzyme activity measured according to, for example, Example 3.

As used herein, "exhibit temperature stability under dry conditions" means residual activity of the lyophilized, glycosylated, modified FAD-GDH itself and when included in a lyophilized composition, calculated and compared to the unstressed lyophilizate after lyophilization and incubation of the lyophilized enzyme at 80° C. for 8 days over molecular sieve (3A, MS551, Grace).

As used herein, "dry conditions" means the test conditions according to Example 7 as set out below, namely the respective lyophilized sample being exposed to 80° C. for 8 days in presence of a drying agent (molecular sieve 3A, MS 551, Grace).

As used herein, "drying agents" means desiccants such as, for example, silica gel, calcium sulfate, calcium chloride, and molecular sieves.

As used herein, "unstressed lyophilizate" means that part of the enzyme that has been lyophilized but not incubated at 80° C. for 8 days over molecular sieve (3A, MS551, Grace). Thus, the unstressed lyophilizate has a temperature stability determined subsequent to lyophilization. This means the unstressed lyophilizate is neither stored nor treated before determining the temperature stability. As noted above, temperature stability under dry conditions may be determined according to Example 7.

Compositions

Glycosylated, modified FAD-GDH Enzymes: Compositions encompassing the inventive concept include isolated, glycosylated, modified FAD-GDHs that have improved temperature stability under dry conditions, as well as variants (i.e., functional equivalents) and active fragments thereof. Briefly, the FAD-GDHs are modified so that at least one of the Asn residues at positions N2, N168 and N346 of mature, wild-type *A. oryzae* FAD-GDH according to SEQ ID NO:2 have been substituted by one or more amino acids not suitable for glycosylation, thereby eliminating or inactivating a potential glycosylation site at one or more of these positions. Moreover, the glycosylated, modified FAD-GDHs as described herein exhibit an improved temperature stability under dry conditions when compared to a reference glycosylated FAD-GDH.

As used herein, "isolated," with respect to a polypeptide (and also a polynucleotide), means a molecule (e.g., polypeptide, protein or polynucleotide) isolated from its natural environment or prepared using synthetic methods such as those known to one of skill in the art. Complete purification is not required in either case. The molecules described herein can be isolated and purified from normally associated material in conventional ways, such that in the purified preparation the molecule is the predominant species in the preparation. At the very least, the degree of purification is such that extraneous material in the preparation does not interfere with use of the molecule in the manner disclosed herein. The molecule is at least about 85% pure; alternatively, at least about 90% pure, alternatively, at least about 95% pure; and alternatively, at least about 99% pure.

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "active fragment(s) thereof" or "functional fragment(s) thereof" mean any modified FAD-GDH as described herein, whereby at least one amino acid is missing in the corresponding sequence according to SEQ ID NOS:3 to 6, provided that such fragments still exhibit the essential properties with respect to enzyme activity and to improved temperature stability under dry conditions.

With respect to the amino acid substitution(s), at least one of the Asn residues at positions N2, N168 and N346 of mature, wild-type *A. oryzae* FAD-GDH according to SEQ ID NO:2 are substituted with one or more amino acids selected from Ala, Arg, Asp, Cys, Gln, Glu, Gly His, Ile, Leu, Lys, Met, Phe, Pro, Ser, Thr, Trp, Tyr, and Val. In some instances, the at least one Asn residue at position N2, N168 and N346 has been substituted by one or more amino acids selected from Arg, Asp, Gln, Glu, Gly His, Lys, Met, Pro, Ser, and Thr. In other instances, the at least one Asn residue at position N2, N168 and N346 are substituted with Ser (S), Pro (P), SerPro (SP) or Asp (D). In certain instances, the substitutions are as follows: N2S (SEQ ID NO:3), N168P (SEQ ID NO:4), N168SP (SEQ ID NO:5) and/or N346D (SEQ ID NO:6). In this context, N168SP means that an Asn residue at position 168 according to SEQ ID NO:2 has been substituted by Ser (S) and Pro (P).

Alternatively, only one of the Asn residues at positions N2, N168 and N346 are substituted with one or more amino acids, which leads to an inactivation (or deletion) of the corresponding glycosylation target site. In other instances, two Asn residues are substituted by one or more amino acids. In still other instances, all three Asn residues are substituted by one or more amino acids.

One of skill in the art understands that the glycosylated, modified FAD-GDHs as described herein may have further modifications different from the above-mentioned substitutions. Consequently, and in certain instances, the glycosylated, modified FAD-GDHs can have a sequence that is a variant or functional equivalent of, for example, SEQ ID NOS:3-6. As used herein, "variant" or "functional equivalent" means an amino acid sequence or molecule that is different in at least one amino acid as provided in one of SEQ ID NOS:3-6, which encodes a protein/enzyme with a same or similar function, in particular in terms of enzyme activity and temperature stability under dry conditions.

Variants of the glycosylated, modified FAD-GDHs are provided that exhibit at least about 70% or more, at least about 75% or more, or at least about 80% or more (e.g., at least about 85% or more, at least about 90% or more, at least about 95% or more, or at least about 99% or more) amino acid sequence identity/sequence homology to the modified FAD-GDHs as described herein, as well as active fragments thereof. Such variants include at least one of more of the same substitution(s) and exhibit essentially the same properties as the glycosylated, modified FAD-GDHs described herein, those essential properties being enzyme activity and improved temperature stability under dry conditions. Likewise, the active fragments of the variants exhibit the same substitution(s) and exhibit essentially the same properties as the glycosylated, modified FAD-GDHs described herein, those essential properties being enzyme activity and improved temperature stability under dry conditions.

Sequence identity of the glycosylated, modified FAD-GDHs, variants and/or active fragments thereof may be determined by the BLAST algorithm, the Basic Local Alignment Search Tool (BLAST). See, Altschul et al. (1990) *J. Mol. Biol.* 215:403-410; and Altschul et al. (1997) *Nucleic Acids Res.* 25:3389-3402. The above-mentioned percentages of amino acid sequence identity refer to the determination of sequence identity by said BLAST algorithm, where the region over which the homology is determined is the entire sequence of a modified FAD-GDH as described herein, and where the sequence of the FAD-GDH is the reference sequence.

With respect to glycosylation, the glycosylated, modified FAD-GDHs, variants and/or functional fragments thereof exhibit a more homogenous glycosylation pattern (with less molecular weight distribution) when compared to a glycosylated FAD-GDH according to SEQ ID NO:1, which is obtained by expression in *A. oryzae*. In some instances, the glycosylated, modified FAD-GDHs, variants and/or functional fragments thereof exhibit a molecular Weight Average Molecular Weight (MW) of about 103 876 and a Number Average Molecular Weight (Mn) of about 99 901. The MW and the Mn can be calculated by means of the software from the raw data of the Viscotek Triple Detektors (refraction index (RI) and Right Angle Light Scattering (RALS)). The ratio of MW/Mn is a polydispersity and gives a size distribution of the molecule. Monodisperse proteins have a MW/Mn value of 1.

In some instances, the glycosylated, modified FAD-GDHs, variants and/or active fragments thereof exhibit a degree of glycosylation of <about 50%, <about 40%, or even <about 30% and/or exhibit a ratio of Mw/Mn of <about 1.02 or <about 1.01 (for calculation of these values, see, e.g., Example 4).

The degree of glycosylation may be calculated according to the following formula:

(Mw(enzyme with glycosylation)−Mw(enzyme according to protein sequence without glycosylation))*100%.

For the enzymes according to Table 2, the following may be calculated (see, Example 4):

FAD-GDH variant 1 (SEQ ID NO:3):

(76333−61461)/61461*100%=24%.

FAD-GDH (SEQ ID NO:1) from *Aspergillus:*

(103876−61592)/61592*100%=69%.

As such, the glycosylated, modified FAD-GDHs, variants and/or active fragments thereof exhibit a more homogenous glycosylation pattern (with less molecular weight distribution) when compared to the glycosylated FAD-GDH according to SEQ ID NO:1, which is obtained by expression in *A. oryzae*. Additionally or alternatively, the glycosylated, modified FAD-GDHs, variants and/or active fragments thereof exhibit a lower degree of glycosylation when compared to the glycosylated FAD-GDH according to SEQ ID NO:1, which is obtained by expression in *A. oryzae*.

The residual activity of a lyophilized, glycosylated, modified FAD-GDH, variant and/or active fragment thereof can be calculated and compared to unstressed lyophilizate after lyophilization and incubation of the lyophilized enzyme at 80° C. for 8 days over molecular sieve (3A, MS551, Grace). In some instances, the residual activity is at least about 80% to at least about 84%. Enzymatic activity may be determined according to, for example, Example 3 (i).

Moreover, the sugar specificity of the glycosylated, modified FAD-GDHs, variants and/or active fragments thereof can be about the same as the sugar specificity of the mature, wild-type FAD-GDH according to SEQ ID No: 2, namely for maltose <about 0.5% and for galactose <about 13%. Sugar specificity may be determined according to, for example, Example 3 (ii).

Modified FAD-GDH-Encoding Nucleic Acid Sequences/ Polynucleotides: Another composition encompassing the inventive concept includes isolated nucleic acid sequences/ polynucleotides (e.g., DNA molecules, RNA molecules or functional equivalent thereof) that encode a glycosylated, modified FAD-GDH, variant or active fragment thereof as described herein with the proviso that the isolated nucleic acid/polynucleotide does not encode SEQ ID NO:2, which is mature, wild-type *A. oryzae* FAD-GDH or does not encode one of the following single substitutions: N168K, N168P, N168Y or N168W. In some instances, the isolated nucleic acid/polynucleotide may be a DNA or RNA molecule or a corresponding gene thereof encoding for one or more substitutions of SEQ ID NOS:3-6.

An isolated polynucleotide has a structure that is not identical to that of any naturally occurring nucleic acid molecule or to that of any fragment of a naturally occurring genomic nucleic acid spanning more than one gene. An isolated polynucleotide also includes, without limitation, (a) a nucleic acid having a sequence of a naturally occurring genomic or extrachromosomal nucleic acid molecule, but which is not flanked by the coding sequences that flank the sequence in its natural position; (b) a nucleic acid incorporated into a vector or into a prokaryote or eukaryote host cell's genome such that the resulting polynucleotide is not identical to any naturally occurring vector or genomic DNA; (c) a separate molecule such as a cDNA, a genomic fragment, a fragment produced by polymerase chain reaction (PCR) or a restriction fragment; and (d) a recombinant nucleotide sequence that is part of a hybrid gene (i.e., a gene encoding a fusion protein). Specifically excluded from this definition are nucleic acids present in mixtures of clones, e.g., as these occur in a DNA library such as a cDNA or genomic DNA library. An isolated polynucleotide can be modified or unmodified DNA or RNA, whether fully or partially single-stranded or double-stranded or even triple-stranded. In addition, an isolated polynucleotide can be chemically or enzymatically modified and can include so-called non-standard bases such as inosine.

The nucleotide sequence of polynucleotides encoding FAD-GDHs from a variety of organisms may be readily obtained from public databases such as, for example, GenBank®, European Nucleotide Archive, DNA Databank of Japan, and Int'l Nucleotide Sequence Database Collaboration. Here, however, an exemplary sequence is SEQ ID NO:2, which is mature, wild-type FAD-GDH from *A. oryzae*.

In particular, the nucleotide sequence is SEQ ID NO:13 or a sequence being substantially complementary to SEQ ID NO:13. Variants or functional equivalents thereof also are contemplated. In some instances, the sequence is an RNA molecule. In other instances, the sequence is a DNA molecule.

As used herein, "RNA molecule" means a linear polymer of ribonucleotide molecules, which is single-stranded and serves as a template for protein synthesis of the glycosylated, modified FAD-GDHs as described herein, especially according to SEQ ID NOS.3-6. Likewise, "DNA molecule" means a linear polymer of deoxyribonucleotide molecules, which is single-stranded as serves as a template for RNA synthesis.

A polynucleotide encoding the glycosylated, modified FAD-GDH, variant or active fragment thereof may be cloned from the genome of respective organisms using PCR or other known technique. Then, mutations may be introduced by techniques such as site-directed mutagenesis, PCR mutagenesis or any other known techniques. The amino acid residue to be mutated may be identified using any software for sequence alignment available in the art. Alternatively, polynucleotides coding for the glycosylated, modified FAD-GDH, variant or active fragment thereof may be prepared by PCR using a series of chemically synthesized oligonucleotides, or fully synthesized.

Expression Vectors and Host Cells: Other compositions encompassing the inventive concept include expression vectors having at least one glycosylated, modified FAD-GDH-encoding polynucleotide or a host cell expressing the vector. As noted above, the polynucleotide, however, does not encode SEQ ID NO:2, which is mature, wild-type *A. oryzae* FAD-GDH or does not encode one of the following single substitutions: N168K, N168P, N168Y or N168W. The glycosylated, modified FAD-GDH may be prepared by inserting a mutant polynucleotide into an appropriate expression vector and introducing the vector into an appropriate host cell, such as, for example, an *Aspergillus* spp. or a *Pichia* spp. The expression vector may be operably linked to a promoter sequence capable of directing its expression in a host cell. It also may include an origin of replication. An exemplary vector is pPICZαA (Invitrogen). This plasmid allows replication in *E. coli* (pUC origin of replication) for cloning of the expression construct, as well as recombinant gene expression in *Pichia pastoris* by using a AOX1 promotor/AOX1 terminator sequences (see, FIG. 1).

In addition, expression vectors may include other nucleotide sequences known in the art such as, for example, signal sequences (for a better folding, transportation into the periplasm or secretion), inducers for a better modulation of the expression, or cleavage sites for cloning. Moreover, the characteristics of the selected expression vector must be compatible to the host cell to be employed. Suitable origins of replications like the ColE1 plasmid replication origin can be used. Suitable promoters include, but are not limited to, lac and trp. Furthermore, it is desirable that the expression vectors include a sequence coding for a selection marker like an antibiotic resistance gene. As selectable markers, ampicillin resistance, or kanamycin resistance may be conveniently employed. All of these materials are known in the art and are commercially available.

Suitable expression vectors containing the desired coding and control sequences may be constructed using standard recombinant DNA techniques known in the art, many of which are described in *Molecular Cloning: A Laboratory Manual*, 3$^{rd}$ ed. (Sambrook et al. eds., Cold Spring Harbor Press 2001); and *Current Protocols in Molecular Biology* (Ausubel et al. eds., John Wiley & Sons 1995).

The recombinant glycosylated, modified FAD-GDH, variant or active fragment thereof thus obtained may be purified by any of the known purification techniques including, but not limited to, ion exchange column chromatography, affinity chromatography, liquid chromatography, filtration, ultra-filtration, salt precipitation, solvent precipitation, immunoprecipitation, gel electrophoresis, isoelectric electrophoresis and dialysis.

In view of the above, another composition encompassing the inventive concept includes host cells incorporating an expression vector as described herein. One of skill in the art understands that such host cells must be capable of glycosylation and therefore include endogenous glycosylating enzymes, particularly for N-linked glycosylation. Consequently, the host cells include an expression vector as described herein with the proviso that the host cells are capable of glycosylation by having endogenous glycosylating enzymes, particularly for N-linked glycosylation.

As used herein, "glycosylating enzymes" mean enzymes that catalyze a reaction in which a carbohydrate (i.e., a glycosyl donor) is attached to a hydroxyl or other functional group of another molecule. This is an enzymatic process that attaches glycans to proteins, lipids or other organic molecules. Glycosylation is a form of co-translational and post-translational modification. The majority of proteins synthesized in the rough ER undergo glycosylation. It is an enzyme-directed, site-specific process, as opposed to the non-enzymatic chemical reaction of "glycation."

As used herein, "host cell capable for glycosylation," particularly for N-linked glycosylation by having endogenous glycosylating enzymes, means a host cell derived from, but not limited to, *Aspergillus* spp. such as *A. niger, A. sojae, A. oryzae*; *Pichia* spp. such as *P. pastoris*; *Saccharomyces cerevisiae*; and *Hansenula polymorpha*. Suitable *Pichia* host cells further include, but are not limited to, *P. pastoris* X33 or *P. pastoris* KM71 H (Invitrogen; Carlsbad, Calif.).

Moreover, one of skill in the art understands that native *E. coli* strains generally lack a glycosylation system and therefore do not express glycosylated proteins. As such, the host cell typically is not an *E. coli* strain. Only if a glycosylation system has been genetically engineered into the *E. coli* (e.g., the N-linked glycosylation system of, for example, *Campylobacter jejuni*), are they enabled to produce glycoproteins.

The host cells typically contain an expression vector as described herein that includes all or part of one of the DNA sequences coding for a modified FAD-GDH, variant and/or active fragment thereof having one or more mutations/substitutions as described herein.

In some instances, the modified FAD-GHD according to SEQ ID NO:1 may be expressed in *A. oryzae* and may be expressed according to the methods as described in, for example, JP Patent No. 2010/239969 and/or US Patent Application Publication Nos. 2009/0259024, 2009/0155848, 2008/0090278, 2008/0020426, 2008/0014612, 2008/0014611, 2008/0003628, as well as U.S. Pat. Nos. 7,871,805, 7,741,100, 7,655,130, 7,553,649 and 7,494,794.

Recombinant production of the glycosylated, modified FAD-GDH as described herein therefore may be conducted in host cells known in the art. In some instances, the suitable host cells can be filamentous fungi such as, for example, *A. niger, A. sojae* and *A. oryzae*. In other instances, the suitable host cells may be strains of yeast such as, for example, *P. pastoris, S. cerevisiae* and *H. polymorpha*. In certain instances, the suitable host cells are *P. pastoris*.

The expression vector(s) may be introduced into the host cells by various methods known in the art. For example, transformation of host cells with expression vectors can be carried out by polyethylene glycol mediated protoplast transformation method (Sambrook et al. (2001), supra). However, other methods for introducing expression vectors into host cells such as, for example, electroporation, ballistic DNA injection or protoplast fusion, also can be employed.

Once the expression vector containing a modified FAD-GDH, variant or active fragment thereof has been introduced into an appropriate host cell, the host cell may be cultured under conditions permitting expression of the desired modified FAD-GDH variant or active fragment thereof. Host cells containing the desired expression vector with the DNA sequence coding for all or part of the modified FAD-GDH can be easily identified by antibiotic selection or complementation of auxotrophic mutants and selection from minimal medium (see, id.). Expression of the modified FAD-GDH, variant or active fragment thereof can be identified by different methods like measuring production of FAD-GDH mRNA transcripts, detection of the gene product immunologically or detection of the enzymatic activity of the gene product. In some intances, an enzymatic assay is applied.

One of skill in the art understands that not all expression vectors and DNA regulatory sequences will function equally well to express the polynucleotides as described herein. Neither will all host cells function equally well with the same expression system. However, one of skill in the art understands how to make an appropriate selection among the expression vectors, DNA regulatory sequences, and host cells using the guidance provided herein without undue experimentation.

Transformants therefore are cultured, and the glycosylated, modified FAD-GDH expressed in the transformant may be collected from the cells or culture medium by any known technique.

As above, recombinant glycosylated, modified FAD-GDH, variant or active fragment thereof thus obtained may be purified by any of the known purification techniques.

Enzyme-Based Compositions: Other compositions encompassing the inventive concept include compositions comprising one or more of the glycosylated, modified FAD-GDHs, variants and/or active fragments thereof or polynucleotides thereof as described herein.

In some instances, the compositions include glycosylated, modified FAD-GDH as described herein or a variant or active fragment thereof and exhibit a molecular weight distribution of the glycosylated, modified FAD-GDH in the composition of a MW of about 103 876 and a Mn of about 99 901.

Thus, the inventive concept encompasses isolated or purified polypeptides, proteins and polynucleotides for a glycosylated, modified FAD-GDH, variant or active fragment thereof as described herein, expression vectors or other constructs including the polynucleotide encoding the glycosylated, modified FAD-GDH, variant or active fragment thereof as described herein, and host cells transformed with such a vector.

Devices

In addition to the above compositions, the inventive concept encompasses various devices for assaying glucose in a sample, where the device includes a glycosylated, modified FAD-GDH, variant or active fragment thereof as described herein, a cofactor (e.g., FAD) and an electron/redox mediator (e.g., quinones, diimines, ferrocene, thionine oxometalates, polymetallophthalocyanines, osmium complexes, ruthenium complexes, pyrroloquinoline quinone, fluorenones, and quinonoid redox dyes such as indamines, phenazines, phenoxazines and phenothiazines.11.

Biosensor Test Strips: One device encompassing the inventive concept includes biosensor test strips having at least the glycosylated, modified FAD-GDH, variant or active fragment thereof as described herein as a reagent. The assay device may have a similar structure as any conventional, commercially available electrochemical (e.g., amperometric) biosensor test strip for monitoring the blood glucose level. One example of such a device has two electrodes (i.e., a working electrode and a reference or counter electrode) positioned on an insulating substrate, a reagent port and a sample receiver. The reagent port contains the glycosylated, modified FAD-GDH, variant or active fragment thereof as described herein and an electron mediator.

When a sample, such as blood sample, is added to the sample receiver, glucose contained in the sample will react with the glycosylated, modified FAD-GDH, variant or active fragment thereof and the electron/redox mediator to generate a current, which is indicative of the amount of glucose in the sample. Examples of electrochemical biosensors for determining enzyme substrates are known in, for example, Int'l Patent Application Publication No. WO 2004/113900 and U.S. Pat. No. 5,997,817.

As an alternative to electrochemical sensors, optical detection technologies might be used. Typically, such optical devices are based on color changes that occur in a reagent system comprising an enzyme, an electron/redox mediator and an indicator. The color changes can be quantified using fluorescence, absorption or remission measurements. Examples of optical devices suited for determining enzyme substrate concentration are known in, for example, U.S. Pat. Nos. 7,008,799; 6,036,919 and 5,334,508.

Enzyme Electrodes: Another device encompassing the inventive concept includes an enzyme electrode having at least the glycosylated, modified FAD-GHD, variant and/or active fragment immobilized on the electrode.

Enzyme Sensors: Another device encompassing the inventive concept includes an enzyme sensor for assaying glucose having an enzyme electrode as described herein as a working electrode. Such sensors can be in the form of test strips to monitor the blood-glucose level in ex vivo samples of, for example, individuals having diabetes. Of course many kinds of samples may be investigated including, but not limited to bodily fluids such as serum, plasma, intestinal fluid or urine. The concentration of glucose in a sample may be determined by measuring the amount of electrons generated by the enzyme reaction. Various sensor systems are known in the art and include, but are not limited to, carbon (C) electrode, metal electrode and Pt electrode.

Here, the glycosylated, modified FAD-GHD, variant and/or active fragment thereof can be immobilized on electrodes. Examples of means for immobilizing molecules include, but are not limited to, cross-linking, encapsulating into a macromolecular matrix, coating with a dialysis membrane, optical cross-linking polymer, electroconductive polymer, oxidation-reduction polymer, and any combination thereof.

When the measurement is conducted in an amperometric system using a C electrode, gold (Au) electrode or Pt electrode provided with an immobilized enzyme is used as a working electrode, together with a counter electrode (such as a Pt electrode) and a reference electrode (such as Ag/AgCl electrode). The electrodes can be inserted into a buffer containing a mediator and kept at predetermined temperature.

A predetermined voltage can be applied to the working electrode, and then a sample is added and an increased value in electric current is measured. Examples of the mediators for use in the assay include, but are not limited to, potassium ferricyanide, ferrocene, osmium derivative, ruthenium derivative, phenazine methosulfate, etc. It is generally also possible to use so-called two-electrode systems with one working electrode and one counter or pseudo-reference electrode.

Further, glucose may be assayed using an immobilized electron mediator in an amperometric system using a C electrode, Au electrode or Pt electrode. The enzyme, such as a glycosylated, modified FAD-GHD, variant and/or active fragment thereof, can be immobilized on the electrode together with an electron/redox mediator in a macromolecular matrix by means of adsorption or covalent bond to prepare a working electrode.

The working electrode can be inserted into buffer together with a counter electrode (such as a Pt electrode) and a reference electrode (such as a Ag/AgCl electrode), and kept at a predetermined temperature. As indicated above, a predetermined voltage can be applied to the working electrode, and then the sample is added and increased value in electric current is measured.

The glycosylated, modified FAD-GDHs, variants and/or active fragments thereof are especially suitable for the use in test strips because they exhibit a more homogeneous glycosylation pattern with less molecular weight distribution, as well as an improved temperature stability under dry condition when compared to known FAD-GDHs.

Likewise, the glycosylated, modified FAD-GDHs, variants and/or active fragments thereof can be used in biosensors for continuous, online monitoring of glucose in a sample or a reactor. See, e.g., D'Costa et al. (1986) *Biosensors* 2:71-87; Laurinavicius et al. (1999) *Anal. Lett.* 32:299-316; Laurinavicius et al. (1999) *Monatshefte fuer Chemie* 130:1269-1281; and Malinauskas et al. (2004) *Sensor Actuat. B-Chem.* 100:395-402. For this purpose, glycosylated, modified FAD-GDHs, variants and/or active fragments thereof as described herein can be used to coat an oxygen-insensitive glassy electrode with an osmium complex containing a redox conductive epoxy network for more accurate determination of the glucose concentration.

Thus, the inventive concept encompasses biosensor test strips, electrodes and sensors including at least the glycosylated, modified FAD-GHD, variant and/or active fragment as described herein.

Kits

In addition to the above compositions and devices, the inventive concept encompasses kits for assaying glucose in a sample, where the kits include at least a glycosylated, modified FAD-GHD, variant and/or active fragment thereof, cofactor and optionally an electron/redox mediator.

Additionally, the kits can include a buffer necessary for the measurement, an appropriate electron mediator and, if necessary, further enzymes such as peroxidase, a standard solution of glucose for preparing a calibration curve and an instruction for use. The glycosylated, modified FAD-GHD, variant and/or active fragment thereof may be provided in various forms such as, for example, a freeze-dried reagent or a solution in an appropriate storage solution.

Any or all of the kit reagents can be provided within containers that protect them from the external environment, such as in sealed containers. Positive and/or negative controls can be included in the kits to validate the activity and correct usage of reagents employed in accordance with the inventive concept. Controls can include samples known to be either positive or negative for the presence of a predetermined concentration of glucose. The design and use of controls is standard and well within the routine capabilities of one of skill in the art.

Methods

Methods of Making or Preparing: In addition to the compositions, devices and kits, the inventive concept encompasses methods of making or preparing glycosylated, modified FAD-GDHs, variants and/or active fragments as described herein.

The methods can include culturing transformed host cells as described above under culture conditions suitable for producing the glycosylated, modified FAD-GDHs, variants and/or active fragments as described herein For bacterial host cells, typical culture conditions are a liquid medium containing carbon and nitrogen sources, the appropriate antibiotic and induction agent (depending on the expression vector used). Appropriate antibiotics include, but are not limited to, ampicillin, kanamycin, chloramphenicol, tetracycline (as well as Zeomycin for *P. pastoris*) and the like. Typical induction agents include, but are not limited to, IPTG, glucose, lactose (for *E. coli*), as well as methanol for *P. pastoris* and the like.

Alternatively, the glycosylated, modified FAD-GDHs, variants and/or active fragments thereof may be obtained by in vitro translation of RNA encoded by a DNA sequence coding for the modified FAD-GDH. For example, the DNA sequences may be synthesized as described above and inserted into a suitable expression vector, which in turn may be used in an in vitro transcription/translation system or other cell-free peptide synthesis system.

Regardless of which method is used, the glycosylated, modified FAD-GDHs, variants and/or active fragments thereof then may be isolated and purified using various routine protein purification techniques as described above. For example, chromatographic procedures such as ion exchange chromatography, gel filtration chromatography and affinity chromatography may be used.

Methods of Using: The inventive concept also encompasses methods of assaying glucose in a body fluid sample by using a glycosylated, modified FAD-GDH, variant and/or active fragment thereof as described herein.

The methods can include at least a step of contacting the sample with a test strip including a glycosylated, modified FAD-GDH, variant and/or active fragment thereof and a step of measuring the amount of the glucose oxidized thereby as described above and further below.

The methods can include the steps described herein, and these steps may be, but not necessarily, carried out in the sequence as described. Other sequences, however, also are conceivable. Furthermore, individual or multiple steps may be carried out either in parallel and/or overlapping in time and/or individually or in multiply repeated steps. Moreover, the methods may include additional, unspecified steps.

Thus, the inventive concept encompasses methods of preparing the glycosylated, modified FAD-GDH, variant and/or active fragment as described herein by culturing the transformant, collecting and purifying the glycosylated, modified FAD-GDH, variant and/or active fragment as described herein from the culture.

SUMMARY

In one aspect, a glycosylated, modified FAD-GDH is provided, where at least one of the Asn residues at positions N2, N168 and N346 of mature, wild-type *A. oryzae* FAD-GDH according to SEQ ID NO:2 are substituted by one or more amino acids not suitable for glycosylation, thereby eliminating or inactivating a potential glycosylation site at one or more of these positions. Also included are variants having at least about 80% or more amino acid sequence identity/homology, as well as active fragments thereof, provided that in the variants or fragments that the substitution(s) eliminating or inactivating the potential glycosylation site(s) is/are preserved when compared to mature, wild-type *A. oryzae* FAD-GDH. Moreover, the variants and/or active fragments exhibit at least about 80% or more of the enzyme activity of the glycosylated, modified FAD-GDHs as described herein and exhibit at least about 80% or more of the temperature stability under dry conditions of the same.

In another aspect, a glycosylated, modified FAD-GDH, variant and/or active fragment thereof is provided that exhibits an improved temperature stability under dry conditions when compared to a glycosylated FAD-GDH according to SEQ ID NO:1, where the FAD-GDH according to SEQ ID NO:1 is obtained by expression in *A. oryzae*.

In another aspect, a glycosylated, modified FAD-GDH, variant and/or active fragment thereof is provided that exhibits a degree of glycosylation that is <about 50% and/or exhibits a ratio of Mw/Mn that is <about 1.02.

In another aspect, a glycosylated, modified FAD-GDH, variant and/or active fragment thereof is provided in which only one of the Asn residues at position N2, N168 and N346 has been substituted by one or more amino acids not suitable for glycosylation, thereby eliminating or inactivating a potential glycosylation site at this position.

In another aspect, a glycosylated, modified FAD-GDH, variant and/or active fragment thereof is provided that has one or more of the following substitutions at positions N2, N168 and N346 of mature, wild-type *A. oryzae* FAD-GDH according to SEQ ID NO:2: N2S, N168P, N168SP, and N346D.

In another aspect, a glycosylated, modified FAD-GDH, variant and/or active fragment thereof is provided having a sequence according to SEQ ID NO:3 (N2S).

In another aspect, a glycosylated, modified FAD-GDH, variant and/or active fragment thereof is provided that exhibits a degree of glycosylation that is <about 50% and/or exhibits a ratio of Mw/Mn that is <about 1.02.

In another aspect, a glycosylated, modified FAD-GDH, variant and/or active fragment thereof is provided with the proviso that it is not mature, wild-type *A. oryzae* FAD-GDH according to SEQ ID NO:2 having a single substitution of N168K, N168P, N168Y or N168W.

In another aspect, an expression vector is provided that includes an isolated polynucleotide as described herein, especially one that does not encode mature, wild-type *A. oryzae* FAD-GDH according to SEQ ID NO:2 having a single substitution of N168K, N168P, N168Y or N168W.

In another aspect, a host cell is provided that includes an expression vector as described herein with the proviso that the host cell is capable of glycosylation, particularly for N-linked glycosylation by having endogenous glycosylating enzymes, and that the host cell is not an *E. coli* strain.

In another aspect, a sensor or a test strip device is provided that includes a glycosylated, modified FAD-GDH, variant and/or active fragment thereof as described herein.

In another aspect, a method of making or producing a glycosylated, modified FAD-GDH, variant and/or active fragment thereof as described herein is provided that includes a step of culturing a transformed host cell as described herein.

In another aspect, a method of detecting, determining or measuring glucose in an ex vivo sample is provided that includes a step of contacting a glycosylated, modified FAD-GDH, variant and/or active fragment thereof as described herein with an ex vivo sample.

In the following examples, all reagents, restriction enzymes, and other materials were obtained from Roche Diagnostics Germany, unless other commercial sources are specified, and used according to the instructions given by the suppliers. Operations and methods employed for the purification, characterization and cloning of DNA are well known in the art (see, e.g., Ausubel et al. (1995), supra) and can be adapted as required by one of skill in the art.

EXAMPLES

The inventive concept will be more fully understood upon consideration of the following non-limiting examples, which are offered for purposes of illustration, not limitation.

Example 1

Expression of Glycosylated, Modified FAD-GDHs

To generate suitable vectors for recombinantly expressing FAD-GDH variants in *P. pastoris*, the synthetic FAD-GDH wild-type gene (SEQ ID NO:7) was ligated into a derivative of plasmid pBluescript SK (Stratagene; La Jolla, Calif.).

In a first step, an intrinsic recognition site for restriction endonuclease XhoI was eliminated by a silent mutation by using a Quick Change II site-directed mutagenesis kit (Stratagene) and primers (SEQ ID NOS:8 and 9) resulting in SEQ ID NO:10.

This construct was used as a template to add flanking sequences including an XhoI site at the 5'-end and an AgeI site at the 3'-end by PCR amplification using PCR primers of SEQ ID NOS:11 and 12. After amplification, the PCR product was hydrolyzed with restriction endonucleases XhoI and AgeI (New England Biolabs) and ligated into the XhoI/AgeI hydrolyzed expression vector pPICZαA (Invitrogen) resulting in a fusion gene (SEQ ID NO:13) coding for the α-factor signal sequence, a proteolytic cleavage site (KEX2) and the mature FAD-GDH.

To introduce a single amino acid substitution, pPICZαA carrying SEQ ID NO:13 was used as a template for site-directed mutagenesis. For the individual substitutions, mutagenic primer pairs as shown in Table 1 were used together with the Quick Change II site-directed mutagenesis Kit (Stratagene) according to the manufacturer's instructions.

TABLE 1

Amino acid substitutions, mutagenic primer pairs and resulting sequences.

| AA Substitution | Mutagenic Primer Pairs | Resulting DNA Sequence |
| --- | --- | --- |
| N2S | SEQ ID NOS: 14 and 15 | SEQ ID NO: 16 |
| N168P | SEQ ID NOS: 17 and 18 | SEQ ID NO: 19 |
| N168SP | SEQ ID NOS: 20 and 21 | SEQ ID NO: 22 |
| N346D | SEQ ID NOS: 23 and 24 | SEQ ID NO: 25 |

To generate the corresponding recombinant expression strains, electrocompetent cells of *P. pastoris* strain X33 (Invitrogen) were transfected by electroporation with 510 μg of linearized pPICZαA carrying the DNA encoding the corresponding FAD-GDH variants (SEQ ID NOS:16, 19, 22 and 25, respectively). All experimental steps were performed according to the manufacturer's instructions. Transfected cells were plated on YPD agar plates (1% yeast extract, 2% peptone, 2% dextrose (glucose)) containing 100 μg/ml, 250 μg/ml or 500 μg/ml Zeocin as a selection marker and incubated at 28° C. for 2-3 days.

To test productivity of the transfected *P. pastoris* clones, a number of single colonies were picked from the selection plates and inoculated in 4 ml of BMMY medium (1% yeast extract, 2% peptone, 100 mM potassium phosphate, pH 6.0, 1.34% yeast nitrogen base (YNB, Invitrogen), 0.0004% biotin). Expression of the recombinant genes was induced by adding 0.5% methanol each day. Cultures were inoculated up to 7 days at 200 rpm and 28° C. Cell density was measured spectrophotometrically (O.D.$_{.600}$). FAD-GDH activity in the supernatants was determined in a spectrophotometric enzyme assay.

Finally, the best producers were transferred into 10 L fermentations to obtain enough material for purification and biochemical characterization of the different FAD-GDH variants.

Example 2

Purification of Glycosylated, Modified FAD-GDHs

1 L blank filtered supernatant from the fermentation was concentrated by ultra filtration/ultra dialysis to 0.05 L and adjusted to pH 7.5 using 20 mM potassium phosphate buffer. Afterwards, the supernatant was adjusted to a 2.5 M concentration of ammonium sulfate by the addition of solid ammonium sulfate.

After incubation about 1 hour at room temperature, the solution was centrifuged and the sediment was discarded. The clear supernatant was applied to a 1000 ml phenyl sepharose column.

After washing the column with 3 L of a 20 mM potassium phosphate buffer pH 7.5 and a ammonium sulfate concentration of 2.5 M, the FAD-GDH was eluted by a linear gradient of a 20 mM potassium phosphate buffer pH 7.5 and a ammonium sulfate concentration of 2.5 M after a 20 mM potassium phosphate buffer pH 7.5 (5 L).

The fractions containing FAD-GDH were collected, purified and concentrated by ultra filtration/ultra dialysis to about 0.05 L and concentrated in 20 mM Tris/HCl buffer pH 8.5. The sample was applied to a 500 ml Q-sepharose column, washed with 2.5 L of a 20 mM Tris/HCl buffer pH 8.5 and eluted by a linear gradient (5 L) of 20 mM Tris/HCl buffer pH 8.5 with 100 mM NaCl. The FAD-GDH-containing fractions were collected, purified and concentrated to a protein concentration of about 50 mg/ml in 100 mM PIPES buffer pH 7.1 by ultra filtration/ultra dialysis. The resulting sample was lyophilized.

Example 3

Enzyme Activity and Sugar Specificity of Glycosylated, Modified FAD-GDHs or Active Fragments Thereof (i) Determining enzyme activity (1M D-glucose as substrate): 50 mM PIPES buffer solution pH 6.5 (including 0.1% Triton X-100), 163 mM PMS solution, 6.8 mM 2,6-dichlorophenol indophenol (DCPIP) solution, 1 M D-glucose solution, 15.6 ml of the aforementioned PIPES buffer, 0.2 ml of DCPIP solution and 4 ml of D-glucose were mixed to make the reaction agent.

(ii) Determining sugar specificity (1M maltose or 1M xylose as substrate): 50 mM PIPES buffer solution pH 6.5 (including 0.1% Triton X-100), 163 mM PMS solution, 6.8 mM 2,6-dichlorophenol indophenol (DCPIP) solution, 1 M D-maltose or D-xylose solution, 15.6 ml of the aforementioned PIPES buffer, 0.2 ml of DCPIP solution and 4 ml of D-maltose or D-xylose solution were mixed to make the reaction agent.

Measurement Conditions for enzyme activity and sugar specificity: 2.9 ml of the respective reaction reagent was pre-heated for 5 minutes at 37° C. 0.1 ml FAD-GDH solution was added and slowly mixed. A spectrometer was calibrated for 5 minutes at 37° C. at 600 nm using water as a reference. The absorbance change per minute ($\Delta OD_{TEST}$)

was determined from the linear portion. As blank test, the absorbance change per minute ($\Delta OD_{BLANK}$) was determined in the same manner as above except that a solvent of the FAD-GDH solution was added to the reagent in place of the FAD-GDH solution.

From the values thus obtained, the FAD-GDH activity was calculated by the following equation. In the present disclosure, one unit (U) of the FAD-GDH activity was defined as the amount of enzyme that reduces 1 μmol of DCPIP per minute in the presence of:

(i) 200 mM D-glucose for determining enzyme activity;

(ii) 200 mM D-maltose or D-xylose for determining sugar specificity.

Activity (U/ml)={-($\Delta OD_{TEST}$-$\Delta OD_{BLANK}$)×3.0×dilution ratio}/{16.3×0.1×1.0}.

In the equation, 3.0 is the amount (ml) of respective reaction reagent+enzyme solution, 16.3 is the millimolar molecular absorption coefficient (cm²/micromole) under the conditions for measuring activities of the present invention, 0.1 is the amount of enzyme solution (ml) and 1.0 is the optical light path (cm) of the cell.

Example 4

Molecular Weight Distribution of Glycosylated, Modified FAD-GDH by SEC-RALS

10 μl of a protein solution having a concentration of about 10 mg/ml in 50 mM potassiumphosphate buffer pH 6.9 with 300 mM NaCl were applied to a G3000SWXL TSKgel column (30 cm; Tosoh Biosep). The flow rate of the HPLC pump was 0.7 ml/min.

For calibration of a Viscotek Triple detector, a freshly prepared solution of bovine serum albumin (Albumin RPLA4, Art.-Nr. 11 726 544; Roche Diagnostics GmbH) was used. A dn/dc value of 0.185 was used for the evaluation of all samples. The evaluation was carried out using the software OmniSEC 4.7.0 (Malvern Instruments). The MW and the Mn was calculated by means of the software from the raw data of the Viscotek Triple Detektors (refraction index (RI) and Right Angle Light Scattering (RALS)). The ratio of MW/Mn is the polydispersity and gives the size distribution of the protein. Monodisperse proteins have a MW/Mn value of 1. Additional details on these methods can be found in, for example, Haney (2004) *LaborPraxis* 28:50-53; Hartmann et al. (2004) *Anal. Biochem.* 325:227-239; and Heinzmann & Tartsch (2004) *GIT Spezial Separation* 27:21-24.

Figure 2:
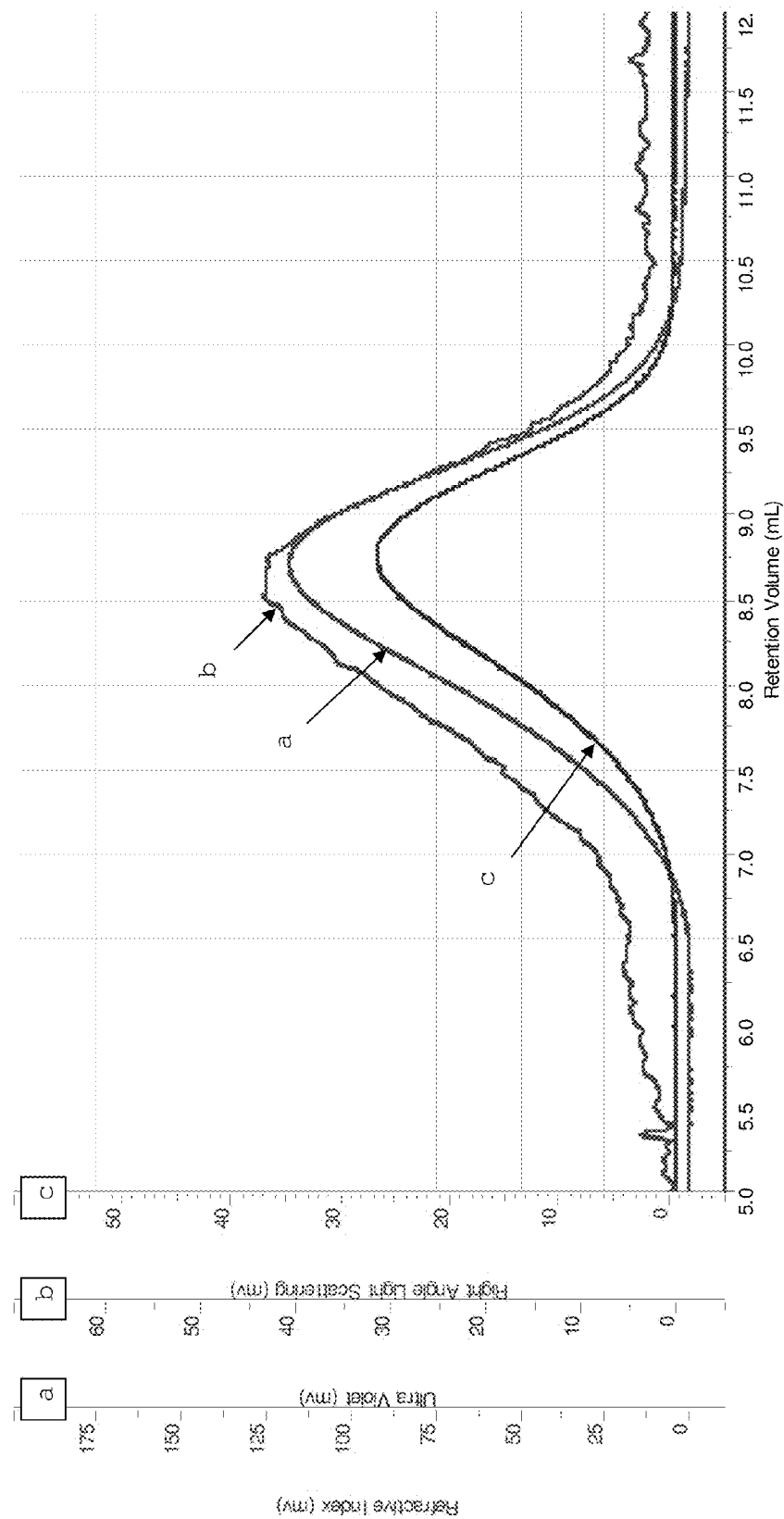
FIG. 2 shows molecular weight distributions of FAD-GDH according to SEQ NO.1 by size-exclusion chromatography-right angle light scattering (SEC-RALS).

Results:

Graph: FAD-GDH (SEQ ID NO:1) from *Aspergillus* are shown in FIG. 2.

Figure 3:
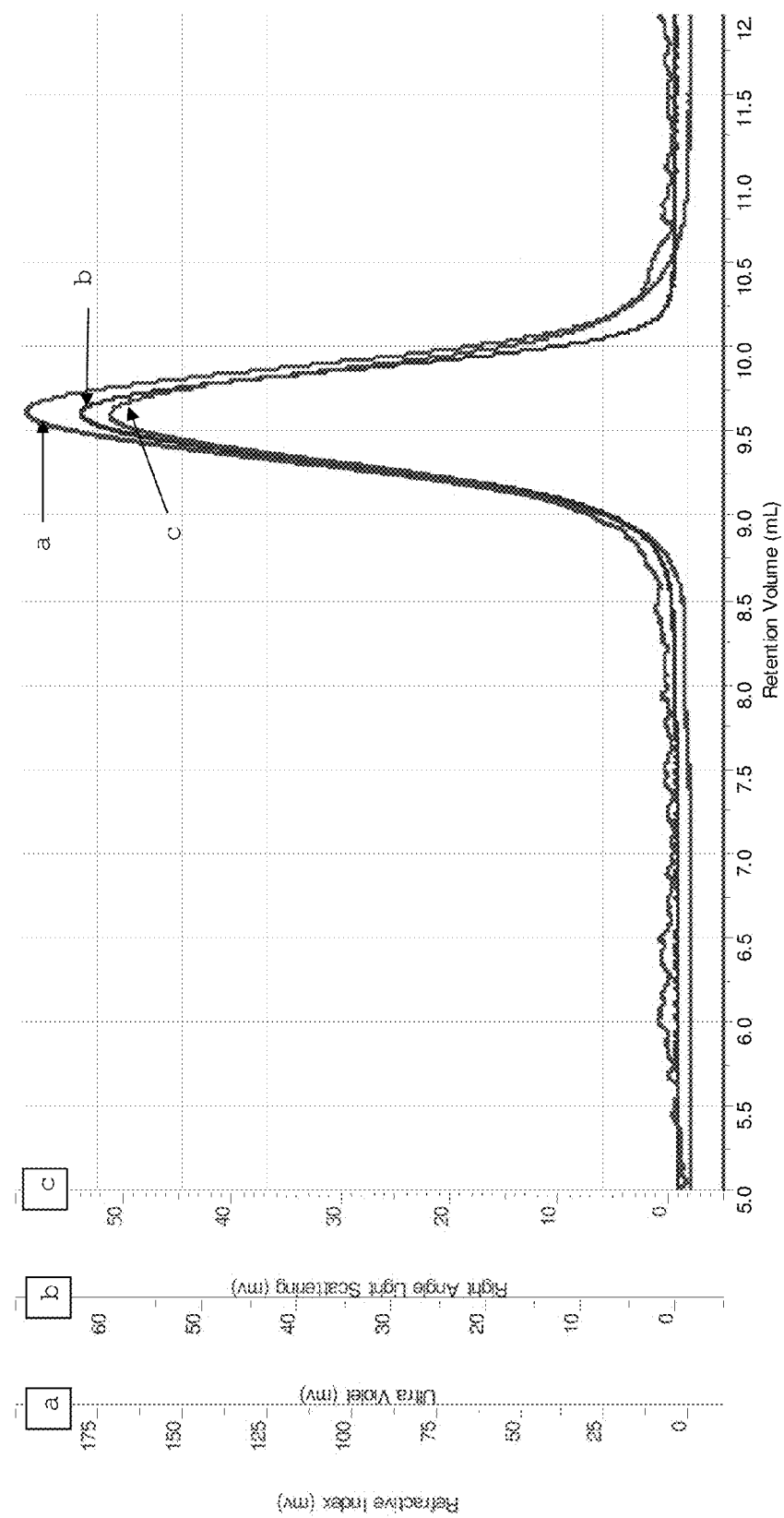
FIG. 3 shows molecular weight distributions of FAD-GDH according to SEQ NO.3 (Variant 1; N2S substitution) by SEC-RALS.

Graph: FAD-GDH (SEQ ID NO:3) variant 1; N2S are shown in FIG. 3.

TABLE 2

| Exemplary molecular weight distribution SEQ ID NO: 1 vs. SEQ ID NO: 3. | | | |
|---|---|---|---|
| Sample Id | $M_w$ | $M_n$ | $M_w/M_n$ |
| FAD-GDH (SEQ ID NO: 1) from *Aspergillus* | 103 876 | 99 901 | 1.040 |
| FAD-GDH (SEQ ID NO: 3) variant 1; N2S | 76 333 | 76 147 | 1.002 |

Example 5

FAD-GDH Activity Assay with a C-Nitrosoanaline Mediator

Solution 1 (S1): 25 mM N,N-bis-(hydroxyethyl)-3-methoxy-nitrosoaniline hydrochloride, (CAS 733686-00-5) with 5% (w/v) PVP (polyvinylpyrrolidone USP K25, FLUKA #81399) in 100 mM Pipes buffer pH 7.1.

Solution 2 (S2): Saturated ~15% (w/v) 2,18 phosphormolybdic acid, sodium salt (($Na_6[P_2Mo_{18}O_{62}]*24H_2O$) CAS 50811-90-0, Honeywell Specialty Chemicals, Article No. 04137) in water.

Solution 3 (S3): 1 M Glucose in water.

Enzyme solution: Dissolve 10 mg/ml lyophilized enzyme in 100 mM Pipes buffer pH 7.1. Dilute this about 1:100 in 100 mM Pipes buffer pH 7.1 to get a rate of 0.02-0.05 ΔE/min.

Measurement procedure:

TABLE 3

| | |
|---|---|
| S1 | 1000 μl |
| S2 | 50 μl |
| S3 | 33 μl |
| Enzyme solution | 50 μl |

Measurement of absorption at 724 nm at 25° C. for 20 min.:

$\epsilon 724$ nm=27.5[mmol$^{-1}$*l*cm$^{-1}$].

KM-values for glucose: The glucose concentration in the reaction mixture was varied in the range of 0.1 mM-170 mM by changing the glucose concentration in S3.

For the calculation of the KM values the measured FAD-GDH activities were fitted to the Michaelis-Menten equation:

$$V = \frac{V_{max} * c}{K_M + c},$$

where
v=measured FAD-GDH activities;
$V_{Max}$=maximal FAD-GDH activity;
KM=Michaelis-Menten constant in mM; and
c=glucose concentration in mM.

Example 6

Temperature Stability in Liquid 10 mg lyophilized enzyme was dissolved per ml 100 mM Pipes buffer pH 7.1. Aliquots of 1 ml of this solution were stored in closed plastic vials and incubated in temperature controlled water baths for up to 12 days. Enzyme activities were measured according to Example 3.

Example 7

Temperature Stability Under Dry Conditions

The unladed weight of the glass vessel was determined by means of an analytical balance. 10 mg of the lyophilized enzyme sample was weighed. All vessels were closed with plugs in a way that a controlled gas exchange of inner space and the environment was ensured but the sample was prohibited from leaving the vessel. The sample was exposed to 80° C. for 8 days in a desiccator in the presence of a drying agent (molecular sieve 3A, MS 551, Grace).

After this period, the sample was cooled to room temperature, further allowing gas exchange with the environment. Afterwards, the vessels were completely closed, and the respective weights were determined. In dependence of the original quantity of enzyme, the sample was diluted with ultrapure water to a final concentration of 10 mg/ml completely dissolved by gentle vortexing. The sample was stored for reconstitution for exactly one hour at room temperature and afterwards cooled with ice. Based on this stock solution, dilution took place in ice-cold working buffer, followed by the determination of activity.

Results:

Reference: FAD-GDH according to SEQ ID NO:1=67+/−5%.

N2S (variant 1): FAD-GDH according to SEQ ID NO:3=79+/−5%.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A glycosylated, modified flavin adenine dinucleotide-dependent glucose dehydrogenase (FAD-GDH) selected from the group consisting of:
   (a). a glycosylated, modified FAD-GDH having at least one asparagine residue selected from the group consisting of N2, N168 and N346 of mature, wild-type *Aspergillus oryzae* FAD-GDH according to SEQ ID NO: 2 substituted by one or more amino acids not suitable for glycosylation, thereby eliminating or inactivating a potential glycosylation site at the at least one asparagine residue with the proviso that the FAD-GDH does not comprise a single asparagine substitution selected from the group consisting of N168K, N168P, N168Y and N168W;
   (b). a glycosylated, modified FAD-GDH having at least 80% amino acid sequence identity or more to the glycosylated, modified FAD-GDH according to (a); and
   (c). an active fragment of the glycosylated, modified FAD-GDH according to (a) or (b), wherein in the glycosylated, modified FAD-GDH according to (b) or the fragment according to (c), the at least one asparagine substitution eliminating or inactivating the potential glycosylation site(s) is preserved when compared to the glycosylated, modified FAD-GDH according to (a), and wherein the glycosylated, modified FAD-GDH according to (b) or the fragment according to (c) exhibits at least 80% of an enzyme activity of the glycosylated, modified FAD-GDH according to (a) and exhibits at least 80% of a temperature stability under dry conditions of the glycosylated, modified FAD-GDH according to (a).

2. The glycosylated, modified FAD-GDH of claim 1, wherein the temperature stability under dry conditions is improved when compared to a glycosylated FAD-GDH according to SEQ ID NO:1 obtained by expression in *A. oryzae*.

3. The glycosylated, modified FAD-GDH of claim 1 further comprising a degree of glycosylation that is at least 50%, and/or a ratio of Mw/Mn that is at least 1.02.

4. The glycosylated, FAD-GDH of claim 1, wherein only one of the asparagine residues selected from the group consisting of N2, N168 and N346 is substituted by one or more amino acids not suitable for glycosylation.

5. The glycosylated, modified FAD-GDH of claim 1, wherein the at least one asparagine residue substitution is selected from the group consisting of a N2S substitution, a N168SP substitution, and a N346D substitution.

6. The glycosylated, modified FAD-GDH of claim 1, wherein the at least one asparagine residue substitution is a N2S substitution and has an amino acid sequence as set forth in SEQ ID NO:3.

7. A composition comprising the glycosylated, modified FAD-GDH or active fragment thereof of claim 1 that exhibits a degree of glycosylation that is at least 50%, and/or a ratio of Mw/Mn that is at least 1.02.

8. An isolated polynucleotide encoding the glycosylated, modified FAD-GDH or active fragment thereof of claim 1 with the proviso that the isolated polynucleotide does not encode mature, wild-type *A. oryzae* FAD-GDH according to SEQ ID NO:2 that has a single asparagine substitution selected from the group consisting of N168K, N168P, N168Y and N168W.

9. An expression vector comprising the isolated polynucleotide of claim 8.

10. A host cell comprising the expression vector of claim 9, wherein the host cell comprises endogenous glycosylating enzymes for N-linked glycosylation, and wherein the host cell is not an *Escherichia coli* strain.

11. A method of making a glycosylated, modified FAD-GDH or an active fragment thereof, the method comprising culturing the transformed host cell of claim 10.

12. A glycosylated, modified FAD-GDH or an active fragment thereof obtained by the method of claim 11.

13. A method of detecting, determining or measuring glucose in an ex vivo sample, the method comprising:
  contacting the glycosylated, modified FAD-GDH or active fragment thereof of claim 1 with the ex vivo sample; and
  detecting, determining or measuring an amount of glucose oxidized by the enzyme.

14. The method of claim 13, wherein the glycosylated, modified FAD-GDH or active fragment is incorporated into reagent of a sensor or a test strip device.

15. The method of claim 13, wherein the glycosylated, modified FAD-GDH or active fragment thereof comprises a N2S substitution, a N168SP substitution and/or a N346D substitution.

16. A device for detecting, determining or measuring glucose in an ex vivo sample comprising the glycosylated, modified FAD-GDH or active fragment thereof of claim 1.

17. The device of claim 16, wherein the glycosylated, modified FAD-GDH or active fragment thereof is incorporated into a reagent composition.

18. The device of claim 16, wherein the glycosylated, FAD-GDH or active fragment thereof is incorporated into a sensor or a test strip device.

* * * * *

SEQUENCE LISTING

```
<160> NUMBER OF SEQ ID NOS: 25

<210> SEQ ID NO 1
<211> LENGTH: 571
<212> TYPE: PRT
<213> ORGANISM: Artificial Sequence
<220> FEATURE:
<223> OTHER INFORMATION: Point mutations of Aspergillus oryzae wild-type
      sequence

<400> SEQUENCE: 1

Lys Asn Thr Thr Thr Tyr Asp Tyr Ile Val Val Gly Gly Gly Thr Ser
1               5                   10                  15

Gly Leu Val Val Ala Asn Arg Leu Ser Glu Asn Pro Asp Val Ser Val
                20                  25                  30

Leu Leu Leu Glu Ala Gly Ala Ser Val Phe Asn Asn Pro Asp Val Thr
            35                  40                  45

Asn Ala Asn Gly Tyr Gly Leu Ala Phe Gly Ser Ala Ile Asp Trp Gln
        50                  55                  60

Tyr Gln Ser Ile Asn Gln Ser Tyr Ala Gly Gly Lys Gln Gln Val Leu
65                  70                  75                  80

Arg Ala Gly Lys Ala Leu Gly Gly Thr Ser Thr Ile Asn Gly Met Ala
                85                  90                  95

Tyr Thr Arg Ala Glu Asp Val Gln Ile Asp Val Trp Gln Lys Leu Gly
                100                 105                 110

Asn Glu Gly Trp Thr Trp Lys Asp Leu Leu Pro Tyr Tyr Leu Lys Ser
            115                 120                 125

Glu Asn Leu Thr Ala Pro Thr Ser Ser Gln Val Ala Ala Gly Ala Ala
        130                 135                 140

Tyr Asn Pro Ala Val Asn Gly Lys Glu Gly Pro Leu Lys Val Gly Trp
145                 150                 155                 160

Ser Arg Ser Leu Ala Ser Gly Asn Leu Ser Val Ala Leu Asn Arg Thr
                165                 170                 175

Phe Gln Ala Ala Gly Val Pro Trp Val Glu Asp Val Asn Gly Gly Lys
            180                 185                 190

Met Arg Gly Phe Asn Ile Tyr Pro Ser Thr Leu Asp Val Asp Leu Asn
        195                 200                 205

Val Arg Glu Asp Ala Ala Arg Ala Tyr Tyr Phe Pro Tyr Asp Asp Arg
    210                 215                 220

Lys Asn Leu His Leu Leu Glu Asn Thr Thr Ala Asn Arg Leu Phe Trp
225                 230                 235                 240
```

```
Lys Asn Gly Ser Ala Glu Glu Ala Ile Ala Asp Gly Val Glu Ile Thr
                245                 250                 255

Ser Ala Asp Gly Lys Val Thr Arg Val His Ala Lys Lys Glu Val Ile
            260                 265                 270

Ile Ser Ala Gly Ala Leu Arg Ser Pro Leu Ile Leu Glu Leu Ser Gly
        275                 280                 285

Val Gly Asn Pro Thr Ile Leu Lys Lys Asn Asn Ile Thr Pro Arg Val
    290                 295                 300

Asp Leu Pro Thr Val Gly Glu Asn Leu Gln Asp Gln Phe Asn Asn Gly
305                 310                 315                 320

Met Ala Gly Glu Gly Tyr Gly Val Leu Ala Gly Ala Ser Thr Val Thr
                325                 330                 335

Tyr Pro Ser Ile Ser Asp Val Phe Gly Asn Glu Thr Asp Ser Ile Val
            340                 345                 350

Ala Ser Leu Arg Ser Gln Leu Ser Asp Tyr Ala Ala Thr Val Lys
        355                 360                 365

Val Ser Asn Gly His Met Lys Gln Glu Asp Leu Glu Arg Leu Tyr Gln
    370                 375                 380

Leu Gln Phe Asp Leu Ile Val Lys Asp Lys Val Pro Ile Ala Glu Ile
385                 390                 395                 400

Leu Phe His Pro Gly Gly Asn Ala Val Ser Ser Glu Phe Trp Gly
                405                 410                 415

Leu Leu Pro Phe Ala Arg Gly Asn Ile His Ile Ser Ser Asn Asp Pro
            420                 425                 430

Thr Ala Pro Ala Ala Ile Asn Pro Asn Tyr Phe Met Phe Glu Trp Asp
        435                 440                 445

Gly Lys Ser Gln Ala Gly Ile Ala Lys Tyr Ile Arg Lys Ile Leu Arg
    450                 455                 460

Ser Ala Pro Leu Asn Lys Leu Ile Ala Lys Glu Thr Lys Pro Gly Leu
465                 470                 475                 480

Ser Glu Ile Pro Ala Thr Ala Ala Asp Glu Lys Trp Val Glu Trp Leu
                485                 490                 495

Lys Ala Asn Tyr Arg Ser Asn Phe His Pro Val Gly Thr Ala Ala Met
            500                 505                 510

Met Pro Arg Ser Ile Gly Gly Val Val Asp Asn Arg Leu Arg Val Tyr
        515                 520                 525

Gly Thr Ser Asn Val Arg Val Val Asp Ala Ser Val Leu Pro Phe Gln
    530                 535                 540

Val Cys Gly His Leu Cys Ser Thr Leu Tyr Ala Val Ala Glu Arg Ala
545                 550                 555                 560

Ser Asp Leu Ile Lys Glu Asp Ala Lys Ser Ala
                565                 570

<210> SEQ ID NO 2
<211> LENGTH: 571
<212> TYPE: PRT
<213> ORGANISM: Aspergillus oryzae

<400> SEQUENCE: 2

Lys Asn Thr Thr Thr Tyr Asp Tyr Ile Val Val Gly Gly Gly Thr Ser
1               5                   10                  15

Gly Leu Val Val Ala Asn Arg Leu Ser Glu Asn Pro Asp Val Ser Val
            20                  25                  30

Leu Leu Leu Glu Ala Gly Ala Ser Val Phe Asn Asn Pro Asp Val Thr
        35                  40                  45
```

```
Asn Ala Asn Gly Tyr Gly Leu Ala Phe Gly Ser Ala Ile Asp Trp Gln
         50                  55                  60

Tyr Gln Ser Ile Asn Gln Ser Tyr Ala Gly Gly Lys Gln Gln Val Leu
 65                  70                  75                  80

Arg Ala Gly Lys Ala Leu Gly Gly Thr Ser Thr Ile Asn Gly Met Ala
                 85                  90                  95

Tyr Thr Arg Ala Glu Asp Val Gln Ile Asp Val Trp Gln Lys Leu Gly
                100                 105                 110

Asn Glu Gly Trp Thr Trp Lys Asp Leu Leu Pro Tyr Leu Lys Ser
                115                 120                 125

Glu Asn Leu Thr Ala Pro Thr Ser Ser Gln Val Ala Ala Gly Ala Ala
        130                 135                 140

Tyr Asn Pro Ala Val Asn Gly Lys Glu Gly Pro Leu Lys Val Gly Trp
145                 150                 155                 160

Ser Gly Ser Leu Ala Ser Gly Asn Leu Ser Val Ala Leu Asn Arg Thr
                165                 170                 175

Phe Gln Ala Ala Gly Val Pro Trp Val Glu Asp Val Asn Gly Gly Lys
                180                 185                 190

Met Arg Gly Phe Asn Ile Tyr Pro Ser Thr Leu Asp Val Asp Leu Asn
        195                 200                 205

Val Arg Glu Asp Ala Ala Arg Ala Tyr Tyr Phe Pro Tyr Asp Asp Arg
        210                 215                 220

Lys Asn Leu His Leu Leu Glu Asn Thr Thr Ala Asn Arg Leu Phe Trp
225                 230                 235                 240

Lys Asn Gly Ser Ala Glu Glu Ala Ile Ala Asp Gly Val Glu Ile Thr
                245                 250                 255

Ser Ala Asp Gly Lys Val Thr Arg Val His Ala Lys Lys Glu Val Ile
                260                 265                 270

Ile Ser Ala Gly Ala Leu Arg Ser Pro Leu Ile Leu Glu Leu Ser Gly
        275                 280                 285

Val Gly Asn Pro Thr Ile Leu Lys Lys Asn Asn Ile Thr Pro Arg Val
        290                 295                 300

Asp Leu Pro Thr Val Gly Glu Asn Leu Gln Asp Gln Phe Asn Asn Gly
305                 310                 315                 320

Met Ala Gly Glu Gly Tyr Gly Val Leu Ala Gly Ala Ser Thr Val Thr
                325                 330                 335

Tyr Pro Ser Ile Ser Asp Val Phe Gly Asn Glu Thr Asp Ser Ile Val
                340                 345                 350

Ala Ser Leu Arg Ser Gln Leu Ser Asp Tyr Ala Ala Thr Val Lys
                355                 360                 365

Val Ser Asn Gly His Met Lys Gln Glu Asp Leu Glu Arg Leu Tyr Gln
        370                 375                 380

Leu Gln Phe Asp Leu Ile Val Lys Asp Lys Val Pro Ile Ala Glu Ile
385                 390                 395                 400

Leu Phe His Pro Gly Gly Asn Ala Val Ser Ser Glu Phe Trp Gly
                405                 410                 415

Leu Leu Pro Phe Ala Arg Gly Asn Ile His Ile Ser Ser Asn Asp Pro
                420                 425                 430

Thr Ala Pro Ala Ala Ile Asn Pro Asn Tyr Phe Met Phe Glu Trp Asp
        435                 440                 445

Gly Lys Ser Gln Ala Gly Ile Ala Lys Tyr Ile Arg Lys Ile Leu Arg
        450                 455                 460
```

```
Ser Ala Pro Leu Asn Lys Leu Ile Ala Lys Glu Thr Lys Pro Gly Leu
465                 470                 475                 480

Ser Glu Ile Pro Ala Thr Ala Ala Asp Glu Lys Trp Val Glu Trp Leu
                    485                 490                 495

Lys Ala Asn Tyr Arg Ser Asn Phe His Pro Val Gly Thr Ala Ala Met
                500                 505                 510

Met Pro Arg Ser Ile Gly Gly Val Val Asp Asn Arg Leu Arg Val Tyr
            515                 520                 525

Gly Thr Ser Asn Val Arg Val Val Asp Ala Ser Val Leu Pro Phe Gln
        530                 535                 540

Val Cys Gly His Leu Val Ser Thr Leu Tyr Ala Val Ala Glu Arg Ala
545                 550                 555                 560

Ser Asp Leu Ile Lys Glu Asp Ala Lys Ser Ala
                565                 570
```

<210> SEQ ID NO 3
<211> LENGTH: 571
<212> TYPE: PRT
<213> ORGANISM: Artificial Sequence
<220> FEATURE:
<223> OTHER INFORMATION: N2S substitution

<400> SEQUENCE: 3

```
Lys Ser Thr Thr Thr Tyr Asp Tyr Ile Val Val Gly Gly Gly Thr Ser
1               5                   10                  15

Gly Leu Val Val Ala Asn Arg Leu Ser Glu Asn Pro Asp Val Ser Val
                20                  25                  30

Leu Leu Leu Glu Ala Gly Ala Ser Val Phe Asn Asn Pro Asp Val Thr
            35                  40                  45

Asn Ala Asn Gly Tyr Gly Leu Ala Phe Gly Ser Ala Ile Asp Trp Gln
50                  55                  60

Tyr Gln Ser Ile Asn Gln Ser Tyr Ala Gly Gly Lys Gln Gln Val Leu
65                  70                  75                  80

Arg Ala Gly Lys Ala Leu Gly Gly Thr Ser Thr Ile Asn Gly Met Ala
                85                  90                  95

Tyr Thr Arg Ala Glu Asp Val Gln Ile Asp Val Trp Gln Lys Leu Gly
                100                 105                 110

Asn Glu Gly Trp Thr Trp Lys Asp Leu Leu Pro Tyr Tyr Leu Lys Ser
            115                 120                 125

Glu Asn Leu Thr Ala Pro Thr Ser Ser Gln Val Ala Ala Gly Ala Ala
        130                 135                 140

Tyr Asn Pro Ala Val Asn Gly Lys Glu Gly Pro Leu Lys Val Gly Trp
145                 150                 155                 160

Ser Gly Ser Leu Ala Ser Gly Asn Leu Ser Val Ala Leu Asn Arg Thr
                165                 170                 175

Phe Gln Ala Ala Gly Val Pro Trp Val Glu Asp Val Asn Gly Gly Lys
                180                 185                 190

Met Arg Gly Phe Asn Ile Tyr Pro Ser Thr Leu Asp Val Asp Leu Asn
            195                 200                 205

Val Arg Glu Asp Ala Ala Arg Ala Tyr Tyr Phe Pro Tyr Asp Asp Arg
        210                 215                 220

Lys Asn Leu His Leu Leu Glu Asn Thr Thr Ala Asn Arg Leu Phe Trp
225                 230                 235                 240

Lys Asn Gly Ser Ala Glu Glu Ala Ile Ala Asp Gly Val Glu Ile Thr
                245                 250                 255
```

Ser Ala Asp Gly Lys Val Thr Arg Val His Ala Lys Lys Glu Val Ile
            260                 265                 270

Ile Ser Ala Gly Ala Leu Arg Ser Pro Leu Ile Leu Glu Leu Ser Gly
            275                 280                 285

Val Gly Asn Pro Thr Ile Leu Lys Lys Asn Asn Ile Thr Pro Arg Val
            290                 295                 300

Asp Leu Pro Thr Val Gly Glu Asn Leu Gln Asp Gln Phe Asn Asn Gly
305                 310                 315                 320

Met Ala Gly Glu Gly Tyr Gly Val Leu Ala Gly Ser Thr Val Thr
                325                 330                 335

Tyr Pro Ser Ile Ser Asp Val Phe Gly Asn Glu Thr Asp Ser Ile Val
            340                 345                 350

Ala Ser Leu Arg Ser Gln Leu Ser Asp Tyr Ala Ala Thr Val Lys
            355                 360                 365

Val Ser Asn Gly His Met Lys Gln Glu Asp Leu Glu Arg Leu Tyr Gln
            370                 375                 380

Leu Gln Phe Asp Leu Ile Val Lys Asp Lys Val Pro Ile Ala Glu Ile
385                 390                 395                 400

Leu Phe His Pro Gly Gly Gly Asn Ala Val Ser Ser Glu Phe Trp Gly
                405                 410                 415

Leu Leu Pro Phe Ala Arg Gly Asn Ile His Ile Ser Ser Asn Asp Pro
            420                 425                 430

Thr Ala Pro Ala Ala Ile Asn Pro Asn Tyr Phe Met Phe Glu Trp Asp
            435                 440                 445

Gly Lys Ser Gln Ala Gly Ile Ala Lys Tyr Ile Arg Lys Ile Leu Arg
450                 455                 460

Ser Ala Pro Leu Asn Lys Leu Ile Ala Lys Glu Thr Lys Pro Gly Leu
465                 470                 475                 480

Ser Glu Ile Pro Ala Thr Ala Ala Asp Glu Lys Trp Val Glu Trp Leu
                485                 490                 495

Lys Ala Asn Tyr Arg Ser Asn Phe His Pro Val Gly Thr Ala Ala Met
            500                 505                 510

Met Pro Arg Ser Ile Gly Gly Val Val Asp Asn Arg Leu Arg Val Tyr
            515                 520                 525

Gly Thr Ser Asn Val Arg Val Val Asp Ala Ser Val Leu Pro Phe Gln
530                 535                 540

Val Cys Gly His Leu Val Ser Thr Leu Tyr Ala Val Ala Glu Arg Ala
545                 550                 555                 560

Ser Asp Leu Ile Lys Glu Asp Ala Lys Ser Ala
                565                 570

<210> SEQ ID NO 4
<211> LENGTH: 571
<212> TYPE: PRT
<213> ORGANISM: Artificial Sequence
<220> FEATURE:
<223> OTHER INFORMATION: N168P substitution

<400> SEQUENCE: 4

Lys Asn Thr Thr Thr Tyr Asp Tyr Ile Val Val Gly Gly Gly Thr Ser
1               5                   10                  15

Gly Leu Val Val Ala Asn Arg Leu Ser Glu Asn Pro Asp Val Ser Val
            20                  25                  30

Leu Leu Leu Glu Ala Gly Ala Ser Val Phe Asn Asn Pro Asp Val Thr
            35                  40                  45

```
Asn Ala Asn Gly Tyr Gly Leu Ala Phe Gly Ser Ala Ile Asp Trp Gln
    50                  55                  60
Tyr Gln Ser Ile Asn Gln Ser Tyr Ala Gly Gly Lys Gln Gln Val Leu
65                  70                  75                  80
Arg Ala Gly Lys Ala Leu Gly Gly Thr Ser Thr Ile Asn Gly Met Ala
                85                  90                  95
Tyr Thr Arg Ala Glu Asp Val Gln Ile Asp Val Trp Gln Lys Leu Gly
            100                 105                 110
Asn Glu Gly Trp Thr Trp Lys Asp Leu Leu Pro Tyr Tyr Leu Lys Ser
            115                 120                 125
Glu Asn Leu Thr Ala Pro Thr Ser Ser Gln Val Ala Ala Gly Ala Ala
    130                 135                 140
Tyr Asn Pro Ala Val Asn Gly Lys Glu Gly Pro Leu Lys Val Gly Trp
145                 150                 155                 160
Ser Gly Ser Leu Ala Ser Gly Pro Leu Ser Val Ala Leu Asn Arg Thr
                165                 170                 175
Phe Gln Ala Ala Gly Val Pro Trp Val Glu Asp Val Asn Gly Gly Lys
            180                 185                 190
Met Arg Gly Phe Asn Ile Tyr Pro Ser Thr Leu Asp Val Asp Leu Asn
        195                 200                 205
Val Arg Glu Asp Ala Ala Arg Ala Tyr Tyr Phe Pro Tyr Asp Asp Arg
    210                 215                 220
Lys Asn Leu His Leu Leu Glu Asn Thr Thr Ala Asn Arg Leu Phe Trp
225                 230                 235                 240
Lys Asn Gly Ser Ala Glu Glu Ala Ile Ala Asp Gly Val Glu Ile Thr
                245                 250                 255
Ser Ala Asp Gly Lys Val Thr Arg Val His Ala Lys Lys Glu Val Ile
            260                 265                 270
Ile Ser Ala Gly Ala Leu Arg Ser Pro Leu Ile Leu Glu Leu Ser Gly
        275                 280                 285
Val Gly Asn Pro Thr Ile Leu Lys Lys Asn Asn Ile Thr Pro Arg Val
    290                 295                 300
Asp Leu Pro Thr Val Gly Glu Asn Leu Gln Asp Gln Phe Asn Asn Gly
305                 310                 315                 320
Met Ala Gly Glu Gly Tyr Gly Val Leu Ala Gly Ala Ser Thr Val Thr
                325                 330                 335
Tyr Pro Ser Ile Ser Asp Val Phe Gly Asn Glu Thr Asp Ser Ile Val
            340                 345                 350
Ala Ser Leu Arg Ser Gln Leu Ser Asp Tyr Ala Ala Ala Thr Val Lys
        355                 360                 365
Val Ser Asn Gly His Met Lys Gln Glu Asp Leu Glu Arg Leu Tyr Gln
    370                 375                 380
Leu Gln Phe Asp Leu Ile Val Lys Asp Lys Val Pro Ile Ala Glu Ile
385                 390                 395                 400
Leu Phe His Pro Gly Gly Asn Ala Val Ser Ser Glu Phe Trp Gly
                405                 410                 415
Leu Leu Pro Phe Ala Arg Gly Asn Ile His Ile Ser Ser Asn Asp Pro
            420                 425                 430
Thr Ala Pro Ala Ala Ile Asn Pro Asn Tyr Phe Met Phe Glu Trp Asp
        435                 440                 445
Gly Lys Ser Gln Ala Gly Ile Ala Lys Tyr Ile Arg Lys Ile Leu Arg
    450                 455                 460
Ser Ala Pro Leu Asn Lys Leu Ile Ala Lys Glu Thr Lys Pro Gly Leu
```

```
            465                 470                 475                 480
Ser Glu Ile Pro Ala Thr Ala Ala Asp Glu Lys Trp Val Glu Trp Leu
                    485                 490                 495

Lys Ala Asn Tyr Arg Ser Asn Phe His Pro Val Gly Thr Ala Ala Met
            500                 505                 510

Met Pro Arg Ser Ile Gly Gly Val Val Asp Asn Arg Leu Arg Val Tyr
                515                 520                 525

Gly Thr Ser Asn Val Arg Val Val Asp Ala Ser Val Leu Pro Phe Gln
                530                 535                 540

Val Cys Gly His Leu Val Ser Thr Leu Tyr Ala Val Ala Glu Arg Ala
545                 550                 555                 560

Ser Asp Leu Ile Lys Glu Asp Ala Lys Ser Ala
                565                 570

<210> SEQ ID NO 5
<211> LENGTH: 572
<212> TYPE: PRT
<213> ORGANISM: Artificial Sequence
<220> FEATURE:
<223> OTHER INFORMATION: N168SP substitution

<400> SEQUENCE: 5

Lys Asn Thr Thr Thr Tyr Asp Tyr Ile Val Val Gly Gly Gly Thr Ser
1               5                   10                  15

Gly Leu Val Val Ala Asn Arg Leu Ser Glu Asn Pro Asp Val Ser Val
                20                  25                  30

Leu Leu Leu Glu Ala Gly Ala Ser Val Phe Asn Asn Pro Asp Val Thr
            35                  40                  45

Asn Ala Asn Gly Tyr Gly Leu Ala Phe Gly Ser Ala Ile Asp Trp Gln
        50                  55                  60

Tyr Gln Ser Ile Asn Gln Ser Tyr Ala Gly Gly Lys Gln Gln Val Leu
65              70                  75                  80

Arg Ala Gly Lys Ala Leu Gly Gly Thr Ser Thr Ile Asn Gly Met Ala
                85                  90                  95

Tyr Thr Arg Ala Glu Asp Val Gln Ile Asp Val Trp Gln Lys Leu Gly
            100                 105                 110

Asn Glu Gly Trp Thr Trp Lys Asp Leu Leu Pro Tyr Tyr Leu Lys Ser
        115                 120                 125

Glu Asn Leu Thr Ala Pro Thr Ser Ser Gln Val Ala Ala Gly Ala Ala
    130                 135                 140

Tyr Asn Pro Ala Val Asn Gly Lys Glu Gly Pro Leu Lys Val Gly Trp
145                 150                 155                 160

Ser Gly Ser Leu Ala Ser Gly Ser Pro Leu Ser Val Ala Leu Asn Arg
                165                 170                 175

Thr Phe Gln Ala Ala Gly Val Pro Trp Val Glu Asp Val Asn Gly Gly
            180                 185                 190

Lys Met Arg Gly Phe Asn Ile Tyr Pro Ser Thr Leu Asp Val Asp Leu
        195                 200                 205

Asn Val Arg Glu Asp Ala Ala Arg Ala Tyr Tyr Phe Pro Tyr Asp Asp
    210                 215                 220

Arg Lys Asn Leu His Leu Leu Glu Asn Thr Thr Ala Asn Arg Leu Phe
225                 230                 235                 240

Trp Lys Asn Gly Ser Ala Glu Glu Ala Ile Ala Asp Gly Val Glu Ile
                245                 250                 255

Thr Ser Ala Asp Gly Lys Val Thr Arg Val His Ala Lys Lys Glu Val
```

```
                260                 265                 270
Ile Ile Ser Ala Gly Ala Leu Arg Ser Pro Leu Ile Leu Glu Leu Ser
            275                 280                 285

Gly Val Gly Asn Pro Thr Ile Leu Lys Lys Asn Asn Ile Thr Pro Arg
            290                 295                 300

Val Asp Leu Pro Thr Val Gly Glu Asn Leu Gln Asp Gln Phe Asn Asn
305                 310                 315                 320

Gly Met Ala Gly Glu Gly Tyr Gly Val Leu Ala Gly Ala Ser Thr Val
            325                 330                 335

Thr Tyr Pro Ser Ile Ser Asp Val Phe Gly Asn Glu Thr Asp Ser Ile
            340                 345                 350

Val Ala Ser Leu Arg Ser Gln Leu Ser Asp Tyr Ala Ala Ala Thr Val
            355                 360                 365

Lys Val Ser Asn Gly His Met Lys Gln Glu Asp Leu Glu Arg Leu Tyr
            370                 375                 380

Gln Leu Gln Phe Asp Leu Ile Val Lys Asp Lys Val Pro Ile Ala Glu
385                 390                 395                 400

Ile Leu Phe His Pro Gly Gly Asn Ala Val Ser Ser Glu Phe Trp
            405                 410                 415

Gly Leu Leu Pro Phe Ala Arg Gly Asn Ile His Ile Ser Ser Asn Asp
            420                 425                 430

Pro Thr Ala Pro Ala Ala Ile Asn Pro Asn Tyr Phe Met Phe Glu Trp
            435                 440                 445

Asp Gly Lys Ser Gln Ala Gly Ile Ala Lys Tyr Ile Arg Lys Ile Leu
            450                 455                 460

Arg Ser Ala Pro Leu Asn Lys Leu Ile Ala Lys Glu Thr Lys Pro Gly
465                 470                 475                 480

Leu Ser Glu Ile Pro Ala Thr Ala Ala Asp Glu Lys Trp Val Glu Trp
            485                 490                 495

Leu Lys Ala Asn Tyr Arg Ser Asn Phe His Pro Val Gly Thr Ala Ala
            500                 505                 510

Met Met Pro Arg Ser Ile Gly Gly Val Val Asp Asn Arg Leu Arg Val
            515                 520                 525

Tyr Gly Thr Ser Asn Val Arg Val Asp Ala Ser Val Leu Pro Phe
            530                 535                 540

Gln Val Cys Gly His Leu Val Ser Thr Leu Tyr Ala Val Ala Glu Arg
545                 550                 555                 560

Ala Ser Asp Leu Ile Lys Glu Asp Ala Lys Ser Ala
            565                 570

<210> SEQ ID NO 6
<211> LENGTH: 571
<212> TYPE: PRT
<213> ORGANISM: Artificial Sequence
<220> FEATURE:
<223> OTHER INFORMATION: N346D substitution

<400> SEQUENCE: 6

Lys Asn Thr Thr Thr Tyr Asp Tyr Ile Val Val Gly Gly Thr Ser
1               5                   10                  15

Gly Leu Val Val Ala Asn Arg Leu Ser Glu Asn Pro Asp Val Ser Val
                20                  25                  30

Leu Leu Leu Glu Ala Gly Ala Ser Val Phe Asn Pro Asp Val Thr
                35                  40                  45

Asn Ala Asn Gly Tyr Gly Leu Ala Phe Gly Ser Ala Ile Asp Trp Gln
```

```
            50                  55                  60
Tyr Gln Ser Ile Asn Gln Ser Tyr Ala Gly Lys Gln Gln Val Leu
 65                  70                  75                  80

Arg Ala Gly Lys Ala Leu Gly Gly Thr Ser Thr Ile Asn Gly Met Ala
                 85                  90                  95

Tyr Thr Arg Ala Glu Asp Val Gln Ile Asp Val Trp Gln Lys Leu Gly
                100                 105                 110

Asn Glu Gly Trp Thr Trp Lys Asp Leu Leu Pro Tyr Tyr Leu Lys Ser
                115                 120                 125

Glu Asn Leu Thr Ala Pro Thr Ser Ser Gln Val Ala Ala Gly Ala Ala
                130                 135                 140

Tyr Asn Pro Ala Val Asn Gly Lys Glu Gly Pro Leu Lys Val Gly Trp
145                 150                 155                 160

Ser Gly Ser Leu Ala Ser Gly Asn Leu Ser Val Ala Leu Asn Arg Thr
                165                 170                 175

Phe Gln Ala Ala Gly Val Pro Trp Val Glu Asp Val Asn Gly Gly Lys
                180                 185                 190

Met Arg Gly Phe Asn Ile Tyr Pro Ser Thr Leu Asp Val Asp Leu Asn
                195                 200                 205

Val Arg Glu Asp Ala Ala Arg Ala Tyr Tyr Phe Pro Tyr Asp Asp Arg
210                 215                 220

Lys Asn Leu His Leu Leu Glu Asn Thr Thr Ala Asn Arg Leu Phe Trp
225                 230                 235                 240

Lys Asn Gly Ser Ala Glu Glu Ala Ile Ala Asp Gly Val Glu Ile Thr
                245                 250                 255

Ser Ala Asp Gly Lys Val Thr Arg Val His Ala Lys Lys Glu Val Ile
                260                 265                 270

Ile Ser Ala Gly Ala Leu Arg Ser Pro Leu Ile Leu Glu Leu Ser Gly
                275                 280                 285

Val Gly Asn Pro Thr Ile Leu Lys Lys Asn Asn Ile Thr Pro Arg Val
                290                 295                 300

Asp Leu Pro Thr Val Gly Glu Asn Leu Gln Asp Gln Phe Asn Asn Gly
305                 310                 315                 320

Met Ala Gly Glu Gly Tyr Gly Val Leu Ala Gly Ala Ser Thr Val Thr
                325                 330                 335

Tyr Pro Ser Ile Ser Asp Val Phe Gly Asp Glu Thr Asp Ser Ile Val
                340                 345                 350

Ala Ser Leu Arg Ser Gln Leu Ser Asp Tyr Ala Ala Ala Thr Val Lys
                355                 360                 365

Val Ser Asn Gly His Met Lys Gln Glu Asp Leu Glu Arg Leu Tyr Gln
                370                 375                 380

Leu Gln Phe Asp Leu Ile Val Lys Asp Lys Val Pro Ile Ala Glu Ile
385                 390                 395                 400

Leu Phe His Pro Gly Gly Gly Asn Ala Val Ser Ser Glu Phe Trp Gly
                405                 410                 415

Leu Leu Pro Phe Ala Arg Gly Asn Ile His Ile Ser Ser Asn Asp Pro
                420                 425                 430

Thr Ala Pro Ala Ala Ile Asn Pro Asn Tyr Phe Met Phe Glu Trp Asp
                435                 440                 445

Gly Lys Ser Gln Ala Gly Ile Ala Lys Tyr Ile Arg Lys Ile Leu Arg
450                 455                 460

Ser Ala Pro Leu Asn Lys Leu Ile Ala Lys Glu Thr Lys Pro Gly Leu
465                 470                 475                 480
```

```
Ser Glu Ile Pro Ala Thr Ala Ala Asp Glu Lys Trp Val Glu Trp Leu
            485                 490                 495

Lys Ala Asn Tyr Arg Ser Asn Phe His Pro Val Gly Thr Ala Ala Met
        500                 505                 510

Met Pro Arg Ser Ile Gly Gly Val Val Asp Asn Arg Leu Arg Val Tyr
            515                 520                 525

Gly Thr Ser Asn Val Arg Val Val Asp Ala Ser Val Leu Pro Phe Gln
        530                 535                 540

Val Cys Gly His Leu Val Ser Thr Leu Tyr Val Ala Glu Arg Ala
545                 550                 555                 560

Ser Asp Leu Ile Lys Glu Asp Ala Lys Ser Ala
            565                 570
```

<210> SEQ ID NO 7
<211> LENGTH: 1716
<212> TYPE: DNA
<213> ORGANISM: Aspergillus oryzae

<400> SEQUENCE: 7

```
aagaacacta cgacatacga ctacatcgtt gtgggaggcg gcacaagtgg tcttgtggtc      60
gcaaatcgcc tttctgagaa ccccgatgtc tccgttcttc tgcttgaggc cggtgcttct     120
gtgttcaaca acccggacgt aaccaacgct aacggttatg gattggcctt ggctcggcc      180
atcgactggc agtaccagtc tattaaccaa agctatgcag gaggtaaaca gcaagttctg     240
cgtgctggta aggcccttgg aggaaccagt acaatcaatg gaatggccta cccgcgca      300
gaggatgtcc agattgacgt ttggcagaaa cttggaaacg aaggttggac gtggaaagat     360
ctcctaccat actacctgaa gagtgaaaac ttgacggccc taccagctc tcaggttgct     420
gctggcgctg cttataaccc tgccgtgaat ggaaaagaag gtcctctcaa ggtcggctgg     480
tcgggaagcc tggcctccgg taatctgtca gttgctctga accgtacgtt ccaagccgct     540
ggtgttccat gggttgagga tgtcaatgga ggcaagatgc gtggcttcaa catctaccca     600
tccacctcg acgttgacct caatgtccgc gaagatgcag cccgggcata ctacttccct     660
tatgatgaca ggaagaacct tcacctgctg agaacacca ctgccaaccg ccttttctgg     720
aagaacggct ctgctgagga agctattgcg gatggtgtcg agatcaccc cgctgatggc     780
aaggtcactc gtgtgcatgc aaagaaagag gtcatcatct ctgctggtgc cctgcggtct     840
cctctcattc tcgagctttc aggagttgga aacccaacca tcctcaaaaa gaacaacata     900
accccacgtg tcgatctccc caccgttggg agaaacctcc aagaccagtt caacaacggc     960
atggctggcg aaggatacgg cgtccttgcc ggtgcctcaa ccgtgaccta cccttccatc    1020
tccgacgtct tcggtaacga gactgactct atcgttgcat ctctccgatc tcaactctcc    1080
gactacgccg ccgcgaccgt caaggtcagc aacgccaca tgaagcagga ggaccttgag    1140
cgcctctacc agctccaatt tgacctcatc gtcaaggaca aggtcccta cgccgagatc    1200
ctcttccacc ccggtggtgg aaacgccgtg tcctccgaat ctggggctt gcttcccttc    1260
gcccgtggca acatccacat tagctccaat gacccgactg ctcccgccgc catcaaccct    1320
aactacttta tgttcgaatg ggacggcaag agccaggccg gtatcgccaa gtacatcagg    1380
aagattctcc gcagcgcacc attgaacaaa cttattgcga aggaaaccaa gcccggtctc    1440
tctgagattc cggccactgc tgcggatgag aagtgggttg aatggctcaa ggctaactat    1500
cgttccaact tccacccgt cggaactgct gccatgatgc ctcgttccat tggtggcgtt    1560
```

```
gttgataacc gtctccgggt ctatggtacc agcaatgttc gcgtcgtaga tgcgtctgtc    1620
ctgcccttcc aggtttgcgg ccacttggtt agcacgcttt atgccgttgc cgagcgcgct    1680
tccgacttga ttaaggagga tgcgaagagt gcttag                              1716

<210> SEQ ID NO 8
<211> LENGTH: 34
<212> TYPE: DNA
<213> ORGANISM: Artificial Sequence
<220> FEATURE:
<223> OTHER INFORMATION: Forward primer - delta-XhoI

<400> SEQUENCE: 8
ggtctcctct cattcttgag ctttcaggag ttgg                                34

<210> SEQ ID NO 9
<211> LENGTH: 34
<212> TYPE: DNA
<213> ORGANISM: Artificial Sequence
<220> FEATURE:
<223> OTHER INFORMATION: Reverse primer - delta-XhoI

<400> SEQUENCE: 9
ccaactcctg aaagctcaag aatgagagga gacc                                34

<210> SEQ ID NO 10
<211> LENGTH: 1716
<212> TYPE: DNA
<213> ORGANISM: Artificial Sequence
<220> FEATURE:
<223> OTHER INFORMATION: Wild-type FAD-GDH XhoI

<400> SEQUENCE: 10
aagaacacta cgacatacga ctacatcgtt gtgggaggcg gcacaagtgg tcttgtggtc    60
gcaaatcgcc tttctgagaa ccccgatgtc tccgttcttc tgcttgaggc cggtgcttct    120
gtgttcaaca ccccggacgt aaccaacgct aacggttatg gattggcctt ggctcggcc    180 atcgactggc agtaccagtc tattaaccaa gctatgcag gaggtaaaca gcaagttctg    240
cgtgctggta aggcccttgg aggaaccagt acaatcaatg gaatggccta cccgcgca    300 gaggatgtcc agattgacgt ttggcagaaa cttggaaacg aaggttggac gtggaaagat    360
ctcctaccat actacctgaa gagtgaaaac ttgacggccc ctaccagctc tcaggttgct    420
gctggcgctg cttataaccc tgccgtgaat ggaaaagaag gtcctctcaa ggtcggctgg    480
tcgggaagcc tggcctccgg taatctgtca gttgctctga accgtacgtt ccaagccgct    540
ggtgttccat gggttgagga tgtcaatgga ggcaagatgc gtggcttcaa catctaccca    600 tccacctcg acgttgacct caatgtccgc gaagatgcag cccgggcata ctacttccct    660
tatgatgaca ggaagaacct tcacctgctg agaacacca ctgccaaccg ccttttctgg    720
aagaacggct ctgctgagga agctattgcg atggtgtcg agatcacctc cgctgatggc    780
aaggtcactc gtgtgcatgc aaagaaagag gtcatcatct ctgctggtgc cctgcggtct    840
cctctcattc ttgagctttc aggagttgga aacccaacca tcctcaaaaa gaacaacata    900
accccacgtg tcgatctccc caccgttggg gagaacctcc aagaccagtt caacaacggc    960
atggctggcg aaggatacgg cgtccttgcc ggtgcctcaa ccgtgaccta cccttccatc    1020
tccgacgtct tcggtaacga gactgactct atcgttgcat ctctccgatc tcaactctcc    1080
gactacgccg ccgcgaccgt caaggtcagc aacggccaca tgaagcagga ggaccttgag    1140
cgcctctacc agctccaatt tgacctcatc gtcaaggaca aggtccctat cgccgagatc    1200
```

```
ctcttccacc ccggtggtgg aaacgccgtg tcctccgaat tctggggctt gcttcccttc    1260
gcccgtggca acatccacat tagctccaat gacccgactg ctcccgccgc catcaaccct    1320
aactacttta tgttcgaatg ggacggcaag agccaggccg gtatcgccaa gtacatcagg    1380
aagattctcc gcagcgcacc attgaacaaa cttattgcga aggaaaccaa gcccggtctc    1440
tctgagattc cggccactgc tgcggatgag aagtgggttg aatggctcaa ggctaactat    1500
cgttccaact tccacccgt cggaactgct gccatgatgc ctcgttccat ggtggcgtt     1560 gttgataacc gtctccgggt ctatggtacc agcaatgttc gcgtcgtaga tgcgtctgtc    1620
ctgcccttcc aggtttgcgg ccacttggtt agcacgcttt atgccgttgc cgagcgcgct    1680
tccgacttga ttaaggagga tgcgaagagt gcttag                             1716

<210> SEQ ID NO 11
<211> LENGTH: 55
<212> TYPE: DNA
<213> ORGANISM: Artificial Sequence
<220> FEATURE:
<223> OTHER INFORMATION: Forward primer

<400> SEQUENCE: 11
atgcctcgag aaaagagagg ctgaagctaa gaacactacg acatacgact acatc          55

<210> SEQ ID NO 12
<211> LENGTH: 96
<212> TYPE: DNA
<213> ORGANISM: Artificial Sequence
<220> FEATURE:
<223> OTHER INFORMATION: Reverse primer

<400> SEQUENCE: 12
gcataccggt cttctcgtaa gtgcccaact tgaactgagg aacagtcatg tctaaggcta    60
caaactcatt aagcactctt cgcatcctcc ttaatc                              96

<210> SEQ ID NO 13
<211> LENGTH: 1971
<212> TYPE: DNA
<213> ORGANISM: Artificial Sequence
<220> FEATURE:
<223> OTHER INFORMATION: FAD-GDH wild-type gene + alpha-factor signal
      sequence and KEX2 site

<400> SEQUENCE: 13
atgagatttc cttcaatttt tactgctgtt ttattcgcag catcctccgc attagctgct     60
ccagtcaaca ctacaacaga agatgaaacg gcacaaattc cggctgaagc tgtcatcggt    120
tactcagatt tagaagggga tttcgatgtt gctgttttgc catttccaa cagcacaaat     180 aacgggttat tgtttataaa tactactatt gccagcattg ctgctaaaga agaaggggta    240
tctctcgaga aaagaaagaa cactacgaca tacgactaca tcgttgtggg aggcggcaca    300
agtggtcttg tggtcgcaaa tcgcctttct gagaaccccg atgtctccgt tcttctgctt    360
gaggccggtg cttctgtgtt caacaacccg gacgtaacca acgctaacgg ttatggattg    420
gcctttggct cggccatcga ctggcagtac cagtctatta ccaaagcta tgcaggaggt    480 aaacagcaag ttctgcgtgc tggtaaggcc cttggaggaa ccagtacaat caatggaatg    540
gcctataccc gcgcagagga tgtccagatt gacgtttggc agaaacttgg aaacgaaggt    600
tggacgtgga aagatctcct accatactac ctgaagagtg aaaacttgac ggcccctacc    660
agctctcagg ttgctgctgg cgctgcttat aaccctgccg tgaatggaaa agaaggtcct    720
```

```
ctcaaggtcg gctggtcggg aagcctggcc tccggtaatc tgtcagttgc tctgaaccgt      780
acgttccaag ccgctggtgt tccatgggtt gaggatgtca atggaggcaa gatgcgtggc      840
ttcaacatct acccatccac cctcgacgtt gacctcaatg tccgcgaaga tgcagcccgg      900
gcatactact tcccttatga tgacaggaag aaccttcacc tgctggagaa caccactgcc      960
aaccgccttt tctggaagaa cggctctgct gaggaagcta ttgcggatgg tgtcgagatc     1020
acctccgctg atggcaaggt cactcgtgtg catgcaaaga aagaggtcat catctctgct     1080
ggtgccctgc ggtctcctct cattcttgag ctttcaggag ttggaaaccc aaccatcctc     1140
aaaaagaaca acataacccc acgtgtcgat ctccccaccg ttggggagaa cctccaagac     1200
cagttcaaca acggcatggc tggcgaagga tacggcgtcc ttgccggtgc ctcaaccgtg     1260 acctacccctt ccatctccga cgtcttcggt aacgagactg actctatcgt tgcatctctc     1320
```
(Note: verifying line 1320 — "acctacccctt" should likely be "acctacccct t" = "acctaccctt" per length)

```
cgatctcaac tctccgacta cgccgccgcg accgtcaagg tcagcaacgg ccacatgaag     1380
caggaggacc ttgagcgcct ctaccagctc caatttgacc tcatcgtcaa ggacaaggtc     1440
cctatcgccg agatcctctt ccaccccggt ggtggaaacg ccgtgtcctc cgaattctgg     1500
ggcttgcttc ccttcgcccg tgcaacatc cacattagct ccaatgaccc gactgctccc     1560
gccgccatca accctaacta ctttatgttc gaatgggacg gcaagagcca ggccggtatc     1620
gccaagtaca tcaggaagat tctccgcagc gcaccattga acaaacttat tgcgaaggaa     1680
accaagcccg gtctctctga gattccggcc actgctgcgg atgagaagtg ggttgaatgg     1740
ctcaaggcta actatcgttc caacttccac cccgtcggaa ctgctgccat gatgcctcgt     1800
tccattggtg gcgttgttga taaccgtctc cgggtctatg gtaccagcaa tgttcgcgtc     1860
gtagatgcgt ctgtcctgcc cttccaggtt tgcggccact tggttagcac gctttatgcc     1920
gttgccgagc gcgcttccga cttgattaag gaggatgcga agagtgctta a            1971
```

<210> SEQ ID NO 14
<211> LENGTH: 35
<212> TYPE: DNA
<213> ORGANISM: Artificial Sequence
<220> FEATURE:
<223> OTHER INFORMATION: Mutagenic primer pair 1

<400> SEQUENCE: 14
ctctcgagaa aagaaagtcc actacgacat acgac                                35

<210> SEQ ID NO 15
<211> LENGTH: 35
<212> TYPE: DNA
<213> ORGANISM: Artificial Sequence
<220> FEATURE:
<223> OTHER INFORMATION: Mutagenic primer pair 1

<400> SEQUENCE: 15
gtcgtatgtc gtagtggact ttcttttctc gagag                                35

<210> SEQ ID NO 16
<211> LENGTH: 1971
<212> TYPE: DNA
<213> ORGANISM: Artificial Sequence
<220> FEATURE:
<223> OTHER INFORMATION: Resulting DNA sequence of mutagenic primer
      pair 1

<400> SEQUENCE: 16
atgagatttc cttcaatttt tactgctgtt ttattcgcag catcctccgc attagctgct      60

```
ccagtcaaca ctacaacaga agatgaaacg gcacaaattc cggctgaagc tgtcatcggt    120
tactcagatt tagaagggga tttcgatgtt gctgttttgc cattttccaa cagcacaaat    180
aacgggttat tgtttataaa tactactatt gccagcattg ctgctaaaga agaagggta     240 tctctcgaga aaagaaagtc cactacgaca tacgactaca cgttgtgggg aggcggcaca    300
agtggtcttg tggtcgcaaa tcgcctttct gagaaccccg atgtctccgt tcttctgctt    360
gaggccggtg cttctgtgtt caacaacccg gacgtaacca acgctaacgg ttatggattg    420
gcctttggct cggccatcga ctggcagtac cagtctatta ccaaagcta tgcaggaggt     480 aaacagcaag ttctgcgtgc tggtaaggcc cttggaggaa ccagtacaat caatggaatg    540
gcctataccc gcgcagagga tgtccagatt gacgtttggc agaaacttgg aaacgaaggt    600
tggacgtgga agatctcct accatactac ctgaagagtg aaaacttgac ggcccctacc     660
agctctcagg ttgctgctgg cgctgcttat aaccctgccg tgaatggaaa agaaggtcct    720
ctcaaggtcg gctggtcggg aagcctggcc tccggtaatc tgtcagttgc tctgaaccgt    780
acgttccaag ccgctggtgt tccatgggtt gaggatgtca atggaggcaa gatgcgtggc    840
ttcaacatct acccatccac cctcgacgtt gacctcaatg tccgcgaaga tgcagcccgg    900
gcatactact tcccttatga tgacaggaag aaccttcacc tgctggagaa caccactgcc    960
aaccgccttt tctggaagaa cggctctgct gaggaagcta ttgcggatgg tgtcgagatc    1020
acctccgctg atggcaaggt cactcgtgtg catgcaaaga aagaggtcat catctctgct    1080
ggtgccctgc ggtctcctct cattcttgag ctttcaggag ttggaaaccc aaccatcctc    1140
aaaaagaaca acataacccc acgtgtcgat ctccccaccg ttggggagaa cctccaagac    1200
cagttcaaca acggcatggc tggcgaagga tacggcgtcc ttgccggtgc ctcaaccgtg    1260
acctaccctt ccatctccga cgtcttcggt aacgagactg actctatcgt tgcatctctc    1320
cgatctcaac tctccgacta cgccgccgcg accgtcaagg tcagcaacgg ccacatgaag    1380
caggaggacc ttgagcgcct ctaccagctc caatttgacc tcatcgtcaa ggacaaggtc    1440
cctatcgccg agatcctctt ccacccggt ggtggaaacg ccgtgtcctc cgaattctgg     1500
ggcttgcttc ccttcgcccg tggcaacatc cacattagct ccaatgaccc gactgctccc    1560
gccgccatca ccctaactta ctttatgttc gaatgggacg gcaagagcca ggccggtatc    1620
gccaagtaca tcaggaagat tctccgcagc gcaccattga caaaactat tgcgaaggaa     1680 accaagcccg gtctctctga gattccggcc actgctgcgg atgagaagtg ggttgaatgg    1740
ctcaaggcta actatcgttc caacttccac cccgtcggaa ctgctgccat gatgcctcgt    1800
tccattggtg gcgttgttga taaccgtctc cgggtctatg gtaccagcaa tgttcgcgtc    1860
gtagatgcgt ctgtcctgcc cttccaggtt tgcggccact tggttagcac gctttatgcc    1920
gttgccgagc gcgcttccga cttgattaag gaggatgcga agagtgctta a             1971
```

<210> SEQ ID NO 17
<211> LENGTH: 30
<212> TYPE: DNA
<213> ORGANISM: Artificial Sequence
<220> FEATURE:
<223> OTHER INFORMATION: Mutagenic primer pair 2

<400> SEQUENCE: 17
gcctggcctc cggtcctctg tcagttgctc                                      30

<210> SEQ ID NO 18

```
<211> LENGTH: 30
<212> TYPE: DNA
<213> ORGANISM: Artificial Sequence
<220> FEATURE:
<223> OTHER INFORMATION: Mutagenic primer pair 2

<400> SEQUENCE: 18
gagcaactga cagaggaccg gaggccaggc                                         30

<210> SEQ ID NO 19
<211> LENGTH: 1971
<212> TYPE: DNA
<213> ORGANISM: Artificial Sequence
<220> FEATURE:
<223> OTHER INFORMATION: Resulting DNA sequence of mutagenic primer
      pair 2

<400> SEQUENCE: 19
atgagatttc cttcaatttt tactgctgtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgttttgc cattttccaa cagcacaaat       180 aacggggttat tgtttataaa tactactatt gccagcattg ctgctaaaga agaagggggta     240 tctctcgaga aaagaaagaa cactacgaca tacgactaca tcgttgtggg aggcggcaca       300
agtggtcttg tggtcgcaaa tgcctttct gagaaccccg atgtctccgt tcttctgctt        360
gaggccggtg cttctgtgtt caacaacccg gacgtaacca acgctaacgg ttatggattg       420
gcctttggct cggccatcga ctggcagtac cagtctatta ccaaagctat gcaggaggt       480 aaacagcaag ttctgcgtgc tggtaaggcc cttggaggaa ccagtacaat caatggaatg       540
gcctataccc gcgcagagga tgtccagatt gacgtttggc agaaacttgg aaacgaaggt       600
tggacgtgga agatctcct accatactac ctgaagagtg aaaacttgac ggcccctacc       660
agctctcagg ttgctgctgg cgctgcttat aaccctgccg tgaatggaaa agaaggtcct       720
ctcaaggtcg gctggtcggg aagcctggcc tccggtcctc tgtcagttgc tctgaaccgt       780
acgttccaag ccgctggtgt tccatggggt gaggatgtca atggaggcaa gatgcgtggc       840
ttcaacatct acccatccac cctcgacgtt gacctcaatg tccgcgaaga tgcagcccgg       900
gcatactact tcccttatga tgacaggaag aaccttcacc tgctggagaa caccactgcc       960
aaccgccttt tctggaagaa cggctctgct gaggaagcta ttgcggatgg tgtcgagatc      1020
acctccgctg atggcaaggt cactcgtgtg catgcaaaga agaggtcat catctctgct      1080 ggtgccctgc ggtctcctct cattcttgag ctttcaggag ttggaaaccc aaccatcctc      1140
aaaaagaaca cataaccccc acgtgtcgat ctccccaccg ttggggagaa cctccaagac      1200
cagttcaaca acggcatggc tggcgaagga tacggcgtcc ttgccggtgc ctcaaccgtg      1260 acctacccttt ccatctccga cgtcttcggt aacgagactg actctatcgt tgcatctctc      1320
cgatctcaac tctccgacta cgccgccgcg acccgtcaagg tcagcaacgg ccacatgaag      1380
caggaggacc ttgagcgcct ctaccagctc caatttgacc tcatcgtcaa ggacaaggtc      1440
cctatcgccg agatcctctt ccaccccggt ggtggaaacg ccgtgtcctc cgaattctgg      1500
ggcttgcttc ccttcgcccg tgcaacatc acattagct ccaatgaccc gactgctccc       1560
gccgccatca accctaacta ctttatgttc gaatgggacg gcaagagcca ggccggtatc      1620
gccaagtaca tcaggaagat tctccgcagc gcaccattga acaaactat tgcgaaggaa      1680 accaagcccg gtctctctga gattccggcc actgctgcgg atgagaagtg ggttgaatgg      1740
```

| ctcaaggcta actatcgttc caacttccac cccgtcggaa ctgctgccat gatgcctcgt | 1800 |
| tccattggtg gcgttgttga taaccgtctc cgggtctatg gtaccagcaa tgttcgcgtc | 1860 |
| gtagatgcgt ctgtcctgcc cttccaggtt tgcggccact tggttagcac gctttatgcc | 1920 |
| gttgccgagc gcgcttccga cttgattaag gaggatgcga agagtgctta a | 1971 |

```
<210> SEQ ID NO 20
<211> LENGTH: 45
<212> TYPE: DNA
<213> ORGANISM: Artificial Sequence
<220> FEATURE:
<223> OTHER INFORMATION: Mutagenic primer pair 3

<400> SEQUENCE: 20
```

| gggaagcctg gcctccggtt ctcctctgtc agttgctctg aaccg | 45 |

```
<210> SEQ ID NO 21
<211> LENGTH: 45
<212> TYPE: DNA
<213> ORGANISM: Artificial Sequence
<220> FEATURE:
<223> OTHER INFORMATION: Mutagenic primer pair 3

<400> SEQUENCE: 21
```

| cggttcagag caactgacag aggagaaccg gaggccaggc ttccc | 45 |

```
<210> SEQ ID NO 22
<211> LENGTH: 1974
<212> TYPE: DNA
<213> ORGANISM: Artificial Sequence
<220> FEATURE:
<223> OTHER INFORMATION: Resulting DNA sequence of mutagenic primer
      pair 3

<400> SEQUENCE: 22
```

| atgagatttc cttcaatttt tactgctgtt ttattcgcag catcctccgc attagctgct | 60 |
| ccagtcaaca ctacaacaga agatgaaacg gcacaaattc cggctgaagc tgtcatcggt | 120 |
| tactcagatt tagaagggga tttcgatgtt gctgttttgc cattttccaa cagcacaaat | 180 |
| aacgggttat tgtttataaa tactactatt gccagcattg ctgctaaaga agaaggggta | 240 |
| tctctcgaga aaagaaagaa cactacgaca tacgactaca tcgttgtggg aggcggcaca | 300 |
| agtggtcttg tggtcgcaaa tgccttttct gagaaccccg atgtctccgt tcttctgctt | 360 |
| gaggccggtg cttctgtgtt caacaacccg gacgtaacca acgctaacgg ttatggattg | 420 |
| gcctttggct cggccatcga ctggcagtac cagtctatta accaaagcta tgcaggaggt | 480 |
| aaacagcaag ttctgcgtgc tggtaaggcc cttggaggaa ccagtacaat caatggaatg | 540 |
| gcctataccc gcgcagagga tgtccagatt gacgtttggc agaaacttgg aaacgaaggt | 600 |
| tggacgtgga aagatctcct accatactac ctgaagagtg aaaacttgac ggcccctacc | 660 |
| agctctcagg ttgctgctgg cgctgcttat aaccctgccg tgaatggaaa agaaggtcct | 720 |
| ctcaaggtcg gctggtcggg aagcctggcc tccggttctc ctctgtcagt tgctctgaac | 780 |
| cgtacgttcc aagccgctgg tgttccatgg gttgaggatg tcaatggagg caagatgcgt | 840 |
| ggcttcaaca tctacccatc caccctcgac gttgacctca atgtccgcga agatgcagcc | 900 |
| cgggcatact acttccctta tgatgacagg aagaaccttc acctgctgga gaacaccact | 960 |
| gccaaccgcc ttttctggaa gaacggctct gctgaggaag ctattgcgga tggtgtcgag | 1020 |
| atcacctccg ctgatggcaa ggtcactcgt gtgcatgcaa agaaagaggt catcatctct | 1080 |

-continued

| | |
|---|---|
| gctggtgccc tgcggtctcc tctcattctt gagctttcag gagttggaaa cccaaccatc | 1140 |
| ctcaaaaaga acaacataac cccacgtgtc gatctcccca ccgttgggga gaacctccaa | 1200 |
| gaccagttca acaacggcat ggctggcgaa ggatacggcg tccttgccgg tgcctcaacc | 1260 |
| gtgacctacc cttccatctc cgacgtcttc ggtaacgaga ctgactctat cgttgcatct | 1320 |
| ctccgatctc aactctccga ctacgccgcc gcgaccgtca aggtcagcaa cggccacatg | 1380 |
| aagcaggagg accttgagcg cctctaccag ctccaatttg acctcatcgt caaggacaag | 1440 |
| gtccctatcg ccgagatcct cttccacccc ggtggtggaa acgccgtgtc ctccgaattc | 1500 |
| tggggcttgc ttcccttcgc ccgtggcaac atccacatta gctccaatga cccgactgct | 1560 |
| cccgccgcca tcaaccctaa ctactttatg ttcgaatggg acggcaagag ccaggccggt | 1620 |
| atcgccaagt acatcaggaa gattctccgc agcgcaccat tgaacaaact tattgcgaag | 1680 |
| gaaaccaagc ccggtctctc tgagattccg gccactgctg cggatgagaa gtgggttgaa | 1740 |
| tggctcaagg ctaactatcg ttccaacttc caccccgtcg gaactgctgc catgatgcct | 1800 |
| cgttccattg gtggcgttgt tgataaccgt ctccgggtct atggtaccag caatgttcgc | 1860 |
| gtcgtagatg cgtctgtcct gcccttccag gtttgcggcc acttggttag cacgctttat | 1920 |
| gccgttgccg agcgcgcttc cgacttgatt aaggaggatg cgaagagtgc ttaa | 1974 |

<210> SEQ ID NO 23
<211> LENGTH: 33
<212> TYPE: DNA
<213> ORGANISM: Artificial Sequence
<220> FEATURE:
<223> OTHER INFORMATION: Mutagenic primer pair 4

<400> SEQUENCE: 23
ccgacgtctt cggtgacgag actgactcta tcg        33

<210> SEQ ID NO 24
<211> LENGTH: 33
<212> TYPE: DNA
<213> ORGANISM: Artificial Sequence
<220> FEATURE:
<223> OTHER INFORMATION: Mutagenic primer pair 4

<400> SEQUENCE: 24
cgatagagtc agtctcgtca ccgaagacgt cgg        33

<210> SEQ ID NO 25
<211> LENGTH: 1971
<212> TYPE: DNA
<213> ORGANISM: Artificial Sequence
<220> FEATURE:
<223> OTHER INFORMATION: Resulting DNA sequence of mutagenic primer
      pair 4

<400> SEQUENCE: 25

| | |
|---|---|
| atgagatttc cttcaatttt tactgctgtt ttattcgcag catcctccgc attagctgct | 60 |
| ccagtcaaca ctacaacaga agatgaaacg gcacaaattc cggctgaagc tgtcatcggt | 120 |
| tactcagatt tagaagggga tttcgatgtt gctgttttgc cattttccaa cagcacaaat | 180 |
| aacggggttat tgtttataaa tactactatt gccagcattg ctgctaaaga agaagggggta | 240 |
| tctctcgaga aaagaaagaa cactacgaca tacgactaca tcgttgtggg aggcggcaca | 300 |
| agtggtcttg tggtcgcaaa tcgcctttct gagaaccccg atgtctccgt tcttctgctt | 360 |
| gaggccggtg cttctgtgtt caacaacccg gacgtaacca acgctaacgg ttatggattg | 420 |

-continued

```
gcctttggct cggccatcga ctggcagtac cagtctatta accaaagcta tgcaggaggt      480
aaacagcaag ttctgcgtgc tggtaaggcc cttggaggaa ccagtacaat caatggaatg      540
gcctataccc gcgcagagga tgtccagatt gacgtttggc agaaacttgg aaacgaaggt      600
tggacgtgga aagatctcct accatactac ctgaagagtg aaaacttgac ggcccctacc      660
agctctcagg ttgctgctgg cgctgcttat aaccctgccg tgaatggaaa agaaggtcct      720
ctcaaggtcg gctggtcggg aagcctggcc tccggtaatc tgtcagttgc tctgaaccgt      780
acgttccaag ccgctggtgt tccatgggtt gaggatgtca atggaggcaa gatgcgtggc      840
ttcaacatct acccatccac cctcgacgtt gacctcaatg tccgcgaaga tgcagcccgg      900
gcatactact tcccttatga tgacaggaag aaccttcacc tgctggagaa caccactgcc      960
aaccgccttt tctggaagaa cggctctgct gaggaagcta ttgcggatgg tgtcgagatc     1020
acctccgctg atggcaaggt cactcgtgtg catgcaaaga aagaggtcat catctctgct     1080
ggtgccctgc ggtctcctct cattcttgag ctttcaggag ttggaaaccc aaccatcctc     1140
aaaaagaaca acataacccc acgtgtcgat ctccccaccg ttggggagaa cctccaagac     1200
cagttcaaca acggcatggc tggcgaagga tacggcgtcc ttgccggtgc ctcaaccgtg     1260
acctacccct ccatctccga cgtcttcggt gacgagactg actctatcgt tgcatctctc     1320
cgatctcaac tctccgacta cgccgccgcg accgtcaagg tcagcaacgg ccacatgaag     1380
caggaggacc ttgagcgcct ctaccagctc caatttgacc tcatcgtcaa ggacaaggtc     1440
cctatcgccg agatcctctt ccacccggt ggtggaaacg ccgtgtcctc cgaattctgg     1500
ggcttgcttc ccttcgcccg tggcaacatc cacattagct ccaatgaccc gactgctccc     1560
gccgccatca accctaacta ctttatgttc gaatgggacg gcaagagcca ggccggtatc     1620
gccaagtaca tcaggaagat tctccgcagc gcaccattga acaaacttat tgcgaaggaa     1680
accaagcccg gtctctctga gattccggcc actgctgcgg atgagaagtg ggttgaatgg     1740
ctcaaggcta actatcgttc caacttccac cccgtcggaa ctgctgccat gatgcctcgt     1800
tccattggtg gcgttgttga taaccgtctc cgggtctatg gtaccagcaa tgttcgcgtc     1860
gtagatgcgt ctgtcctgcc cttccaggtt tgcggccact tggttagcac gctttatgcc     1920
gttgccgagc gcgcttccga cttgattaag gaggatgcga agagtgctta a              1971
```